US006787641B1

(12) United States Patent
Greenwald et al.

(10) Patent No.: US 6,787,641 B1
(45) Date of Patent: Sep. 7, 2004

(54) IDENTIFICATION OF SEL-12 AND USES THEREOF

(75) Inventors: Iva Greenwald, New York, NY (US); Diane Levitan, Tenafly, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/043,944

(22) PCT Filed: Sep. 27, 1996

(86) PCT No.: PCT/US96/15727

§ 371 (c)(1),
(2), (4) Date: Oct. 6, 2000

(87) PCT Pub. No.: WO97/11956

PCT Pub. Date: Apr. 3, 1997

Related U.S. Application Data

(60) Provisional application No. 60/004,387, filed on Sep. 27, 1995.

(51) Int. Cl.$^7$ .............................................. C07H 21/02
(52) U.S. Cl. .................. 536/23.1; 435/69.1; 435/320.1; 435/252.3; 435/325; 435/640; 435/455; 435/471; 530/350; 514/2; 514/44; 424/93.6; 424/93.7
(58) Field of Search ........................ 536/23.1; 530/350; 514/2, 44; 435/69.1, 320.1, 252.3, 325, 440, 455, 471; 424/93.6, 93.7

(56) References Cited

U.S. PATENT DOCUMENTS

| 5,840,540 A | 11/1998 | St. George-Hyslop et al. |
| 5,986,054 A | * 11/1999 | St. George-Hyslop et al. ........................... 530/350 |
| 6,087,153 A | 7/2000 | Greenwald et al. |
| 6,376,239 B1 | 4/2002 | Baumeister |

OTHER PUBLICATIONS

Daigle I., and Li C., "apl–1, a *Caenorhabditis elegans* gene encoding a protein related to the human beta–amyloid protein precursor" Proc. Natl. Acad. Sci. U.S.A. (1993) 90(24):12045–9 (Exhibit 4).
Database dbEST, National Center for Biotechnology Information, National Library of Medicine, GenBank Accession No. H19012 (1995) (Exhibit 5).
Database EMBL Accession No. U35660 (1995) Levitan D., Greenwald I., "*Caenorhabditis elegans* membrane protein (sel–12) mRNA " XPoo2176178 (Exhibit 6).
Fire A., et al., "A modular set of lacz fusion vectors for studying gene expression in Caenorhabditis elegans" Gene (1990) 93(2):189–98 (Exhibit 7).
Fitgerald K., and Greenwald I., "Interchangeability of Caenorhabditis elegans DSL proteins and intrinsic signalling activity of their extracellular domains in vivo" Development (1995) 121(12):4275–82 (Exhibit 8).

Greenwald I., "Structure/function studies of lin–12/Notch proteins" Curr. Opin. Genet. Dev. (1994) 4(4):556–62 (Exhibit 9).
Hedegecock E. M. and Herman R. K., "The ncl–1 gene and genetic mosaics of Caenorhabditis elegans" Genetics (1995) 141 (3):989–1006 (Exhibit 10).
Hedegecock E. M., et al., "Genetics of cell and axon migrations in Caenorhabditis elegans" Development (1987) 100 (3): 365–82 (Exhibit 11).
Levitan D. and Greenwald I., "Facilitation of lin–12–mediated signalling by sel–12, a Caenorhabditis elegans S182 Alzheimer's disease gene" Nature (1995) 377 (6547): 351–4 (Exhibit 12).
Levy–Lahad E., et al., "Genomic structure and expression of SSTM2, the chromosome 1 familial Alzheimer disease gene" Genomics (1996) 34(2):198–204 (Exhibit 13).
Li X. and Greenwald I., "HOP–1, a Caenorhabditis elegans presenilin, appears to be functionally redundant with SEL–12 presenilin and to facilitate LIN–12 and GLP–1 signaling " Proc. Natl. Acad. Sci. U.S.A. (1997) 94(22):12204–9 (Exhibit 14).
Rogaev E. I., et al., "Familial Alzheimer's disease in kindreds with missense mutations in a gene on chromosome 1 related to the Alzheimer's disease type 3 gene" Nature (1995) 376(6543):775–8 (Exhibit 15).
Sherrington R., et al., "Cloning of a gene bearing missense mutations in early–onset familial alzheimer's disease" Nature (1995) 375(6534):754–60 (Exhibit 16).
Stratagene Cloning Systems Catalog, 1993 pp. 27, 31, 32, and 313 (Exhibit 17).
Sundaram M. and Greenwald I., "Genetic and phenotypic studies of hypomorphic lin–12 mutants in Caenorhabditis elegans" Genetics (1993) 135(3):755–63 (Exhibit 18).
Sundaram M. and Greenwald I., "Suppressors of a lin–12 hypomorph define genes that interact with both lin–12 and glp–1 in Caenorhabditis elegans" Genetics (1993) 135(3):765–83 (Exhibit 19).

(List continued on next page.)

*Primary Examiner*—Robert A. Wax
*Assistant Examiner*—Samuel W. Liu
(74) *Attorney, Agent, or Firm*—John P. White; Cooper & Dunham LLP

(57) ABSTRACT

This invention provides an isolated nucleic acid molecule encoding a SEL-12. This invention further provides an isolated nucleic acid molecule which encodes a mutated SEL-12. This invention also provides an isolated nucleic acid molecule which encodes a mutated SEL-12, wherein the mutated SEL-12 contains at least one of the following: position 115 is a leucine, position 132 is an arginine, position 215 is a glutamic acid, position 229 is a valine, position 254 is a valine, position 255 is a valine, position 371 is a valine, position 387 is a tyrosine, position 104 is an isoleucine or position 204 is a valine, This invention further provides different uses of these nucleic acid molecules. This invention also provides different sel-12 mutants and transgenic animals which carry wild-type or mutated sel-12.

13 Claims, 5 Drawing Sheets

OTHER PUBLICATIONS

Wen C., et al., "spr–2, a suppressor of the egg–laying defect caused by loss of sel–12 presenilin in Caenorhabditis elegans, is a member of the SET protein subfamily" Proc. Natl. Acad. Sci. U.S.A. (2000) 97(26):14524–9 (Exhibit 20).

Wilkinson H. A. and Greenwald I., "Spatial and temporal patterns of lin–12 expression during C. elegans hermaphrodite development" Genetics 1995 141(2):513–26 (Exhibit 21); and.

Wilkinson H. A., et al., "Reciprocal changes in expresssion of the receptro lin–12 and its ligand lag–2 prior to commitment in a C. elegans cell fate decsion" Cell (1994) 79(7):1187–98 (Exhibit 22).

Brenner S., "The genetics of Caenorhabditis elegans", Genetics. (1974) 77(1):71–94 (Exhibit 1).

Levy–Lahad E., et al., "Candidate gene for the chromosome 1 familial Alzheimer's disease locus" Science (1995) 269 (5226):973–7 (Exhibit 2).

L'Hernault S. W. and Arduengo P. M., "Mutation of a putative sperm membrane protein in Caenorhabditis elegans prevents sperm differentiation but not its associated meiotic divisions" J. Cell. Biol. (1992) 119(1):55–68 (Exhibit 3).

Mello C. C., et al., "Efficient gene transfer in C.elegans: extrachromosomal maintenance and integration of transforming sequences" EMBO. J. (1991) 10(12): 3959–70 (Exhibit 4).

Struhl G., et al., "Intrinsic activity of the Lin–12 and Notch intracellular domains in vivo" Cell (1993) 74(2):331–45 (Exhibit 5).

European Search Report, dated Nov. 20, 2002 (Exhibit 2).

PCT International Search Report, dated Jan. 21, 1997 (Exhibit 3).

PCT Written Opinion, dated Jul. 15, 1997 (Exhibit 4).

Data Base Search, total of 3 pages (Exhibit 5).

Bai, C. et al., "SKP1 connects cell cycle regulators to the ubiquitin proteolysis machinery through a novel motif, the F–box," Cell 86:263–74 (1996) (Exhibit 6).

Ellisen, L. W. et al., "TAN–1, the human homolog of the Drosophila Notch gene, is broken by chromosomal translocations in T lymphoblastic neoplasms," Cell 66:649–61 (1991) (Exhibit 7).

Gallahan, D. and Callahan, P., "Mammary tumorigneesis in feral mice: identification of a new int locus in mouse mammary tumor virus (Czech II)—induced mammary tumors," J. Virol. 61:66–74 (1987) (Exhibit 8).

Grant, B. and Greenwald, I., "Structure, function and expression of SEL–1, a negative regulatro of LIN–2 and GLP–in C. elegans," Development 124:637–644 (1997).

Greenwald, I. et al., "The lin–12 locus specifies cell fates in C. elegans," Cell 34:435–44 (1983) (Exhibit 10).

Greenwald, I. and Seydoux, G., "Analysis of gain–of–function mutaitons of the lin–2 gene of C. elegans," Nature 346:197–99 (1990) (Exhibit 11).

Hubbard, J. et al., "Sel–10 negative regulator of lin–12 activity in C. elegans, encodes a member of the CDC4 family of proteins," Genes Dev. 11:3182–93 (1997) (Exhibit 12).

Kimble, J., "Alteration in cell lineage following laser ablation of cells in the somatic gonad of C. elegans," Dev. Biol. 87:286–300 (1981) (Exhibit 13).

King, R.W. et al, "How proteolysi drives the cell cycle," Science 274:1652–58 (1996) (Exhibit 14).

Neer, E.J. et al., "The ancient regulatory–protein family of WD–repeat proteins," Nature 371:296–300 (1994).

Robbins, J. et al. "Mouse mammary tumor gen int–3: a member of the Notch gene family transforms mammary epithelial cellls," J. Virol. 66:2594–99 (1992) (Exihibit 16).

Seydoux, G. and Greenwald, I., "Cell autonomy of lin–12 function in a cell fate decision in C. elegnas," Cell 57:1237–45 (1989) (Exhibit 17).

Shen, J. et al, "Skeletal and CNS defects in presenilin–1–deficient mice," Cell 89:629–39 (1997) (Exhibit 18).

Sherrington, R. et al., "Cloning of a gene bearing missense mutations in early–onset familial Alzheimer's disease," Nature 375:754–60 (1995) (Exhibit 19).

Sundaram, M. and Greenwald, I., "Genetic and phenotypic studies of hypomorphic lin–12 mutants in C. elegans," Genetics 135:755–63 (1993) (Exhibit 20).

Tuck, S. and Greenwald, I., "Lin–25, a gene required for vulval induction in C. elegans," Gmes Dev. 9:341–57 (1995) (Exhibit 21).

Wilson, R. et al., "2.2 Mb of contiguous nucleotide sequence from chromosome III of C. elegans," Nature 368:32–38 (1994) (Exhibit 22).

Wong, P.C. et al., "Presenilin–1 is required for Notch1 and Dll 1 expression in the paraxial mesoderm," Nature 387:288–91 (1997) (Exhibit 23); and.

Yochem, J. and Byers, B., "Structural comparison of the yeast cell division cycle gene CDC4 and a related pseudogene," J. Mol. Biol. 195:233–45 (1987) (Exhibit 24).

* cited by examiner

FIGURE 1A

```
   1 GTTTAATTACCCAAGTTTGAGATGCCTTCCACAAGGAGACAACAGGAGGGCGGAGTTGCAGATGCGGAAACACAtACCGTTTACGGTACAAATCTGATAA     100
   1                  M  P  S  T  R  R  Q  Q  E  G  G  G  A  D  A  E  T  H  T  V  Y  G  T  N  L  I  T     27
 101 CAAATCGGAATAGCCAAGAACGAAAATGTTGTGGAAGAAGCGGAGCTGAAATACGGAGCATCTCACGTTATTCATCTTATTTGTCCCGTTGTCACTATG     200
  28  N  R  N  S  Q  E  D  E  N  V  V  E  E  A  E  L  K  Y  G  A  S  H  V  I  H  L  F  V  P  V  S  L  C     60
 201 CATGGCTCTCGTTGTTTTACGATGAACACGATTACGTTTTATAGTCAAAACAATGGAAGGCATTtACTATCACATCCTTTTGTCCGGAAACAGACAGT     300
  61  M  A  L  V  V  F  T  M  N  T  I  T  F  Y  S  Q  N  N  G  R  H  L  L  S  H  P  F  V  R  E  T  D  S     93
 301 ATCGTTGAGAAGGGATTGATGTCACTTGGAAATGCTCTCGTCATGTTGTGCGTGGTCGTTCTGATGACAGTTCTGATTGTTTTCTATAAATACAAGT     400
  94  I  V  E  K  G  L  M  S  L  G  N  A  L  V  M  L  C  V  V  L  M  T  V  L  I  V  F  Y  K  Y  K       126
 401 TTTATAAGCTTATTCATGGATGCTTATTGTCAGCAGTTTTCTTCTTCTTTGTCACTACAATCTATGTGCaAGAAGTTCTGAAAAGTTTCGATGT       500
 127  F  Y  K  L  I  H  G  W  L  I  V  S  S  F  L  L  F  L  F  T  T  I  Y  V  Q  E  V  L  K  S  F  D  V    160
 501 GTCTCCAGCGCCACTATTGTTTTGTTTGGACTGGGTAACTATGGAGTTCTCGGAATGATGTGTATACATTGGAAAGGTCCATTGCGTCTGCAACAGTTC    600
 161  S  P  S  A  L  L  V  L  F  G  L  G  N  Y  G  V  L  G  M  M  C  I  H  W  K  G  P  L  R  L  Q  Q  F    193
 601 TACCTTATTACAATGTCTGCACTAATGGCTCTGGTCTTTATCAAGTACCTACCAGAATGGACTGTGTGGTTTGTGCTGTTTGTATCGGTTTGGATC        700
 194  Y  L  I  T  M  S  A  L  M  A  L  V  F  I  K  Y  L  P  E  W  T  V  W  F  V  L  F  V  I  S  V  W  D  L  227
 701 TGGTTGCCGTGCTCACACCAAAAGGACCATTGGTGAACTGCACAGAGAGAAACAGCCAATTTCCCGGCGCTGATTATTCGtCTGG              800
 228  V  A  V  L  T  P  K  G  P  L  R  Y  L  V  E  T  A  Q  E  R  N  E  P  I  F  P  A  L  I  Y  S  S  G    260
 801 AGTCATCTATCCCTACGTTCTTGTTACTGCAGTTGAAAACACGACAGACCCCGTGAACCGACGTGTCAGACTCAAATaCTTCTACAGCTTTTCCTGA      900
 261  V  I  Y  P  Y  V  L  V  T  A  V  E  N  T  T  D  P  R  E  P  T  S  S  D  S  N  T  S  T  A  F  P  G    293
 901 GAGGCGAGTTGTTCATCTGAAACGGCCAAAGTCCAAAATGTCGAATGAATCGAATACAGCTTCAAGCACACAAA                          1000
 294  E  A  S  C  S  S  E  T  P  K  R  P  K  V  K  R  I  P  Q  K  V  Q  I  E  S  N  T  T  A  S  T  Q  N    327
1001 ACTCTGGAGTAAGGGTGAACGGGAGCTAGCTGCTGAGAGACCAACTGTACAAGACGCCAATTTCTACAGGCAACGACTACTTGACTGGAAGAGAAGGTGAAACT 1100
 328  S  G  V  R  V  E  R  E  L  A  A  E  R  P  T  V  Q  D  A  N  F  H  R  H  E  E  E  R  G  V  K  L      360
1101 TGGTCTGGGCGACTTCATTTCTACTCTGTTCTCCTCGGCAAGGCTTCAAATGAACAGACTACTTGCTTGTTATGTGGCCATTCTTATC            1200
 361  G  L  G  D  F  I  F  Y  S  V  L  L  G  K  A  S  S  Y  F  D  W  N  T  T  I  A  C  Y  A  L  L  I      393
1201 GGTCTCTGCTTCACTCTTGTCCTGCTGGCCGTCTTCAAACGAGCACTCCCGGCTCTGCAATTTCCATTTCTCCGGACTCATTTTTTACTTTTGTACCCG    1300
 394  G  L  C  F  T  L  V  L  L  A  V  E  K  R  A  L  P  A  L  Q  F  P  F  S  P  D  S  F  F  T  F  V  P  A  427
1301 CTGGATCATCACCCCATTTGTTACACAAGTCTCTCAAAGTGTTTATTATATTAATTCTCTGTTTTTGCCATTTCTTTGCATCATCAACTTTCGATTAT    1400
 428  G  S  S  P  H  L  L  H  K  S  L  K  S  V  Y  Y  I  N  S  L  F  L  P  F  L  C  I  I  N  F  S  I  I    460
1401 ATCTTGAGCGATCTCAAAGCTTTATTTTACATACCTATTTATTTTTGAACTTTGTCATTTAAGTTATATAATAATTTATTAAAAAAAAAAAAAA        1500
 461  S  *                                                                                              
```

FIGURE 2A

```
SEL-12  ..........  ..........  ..........  ..........  ..MPSTRRQQ
  S182  .....MTEIP  APLSYFQNAQ  MSEDNHLSNT  VRSQNDNRER  QEH.NDRRSL
  E5-1  MLTFMASDSE  EEVCDERTSL  MSAESPTPRS  CQEGRQGPED  GENTAQWRSQ

SEL-12  EGGGADAETH  TVYGTNLITN  RNSQEDENVV  EEAELKYGAS  HVIHLFVPVS
  S182  GHPEPLSNGR  PQGNSRQVVE  QDEEED....  EELTLKYGAK  HVIMLFVPVT
  E5-1  ENEEDGEEDP  DRYVCSGVPG  RPPGLE....  EELTLKYGAK  HVIMLFVPVT
 SPE-4  ..........  ..........  ...MDTLRSI  SSELVRSSQL  RWTLFSVIAN

TM1
        ----------------
         *                                                    X
SEL-12  LCMALVV.FT  MNTITFYSQN  NGRHLLSHPF  VRETDSIVEK  GLMSLGNALV
  S182  LCMVVVV.AT  IKSVSFYTRK  DG.QLIYTPF  TEDTETVGQR  ALHSILNAAI
  E5-1  LCMIVVV.AT  IKSVRFYTEK  NG.QLIYTPF  TEDTPSVGQR  LLNSVLNTLI
 SPE-4  MSLTLSIWIG  VYNMEVNSEL  SKTYFLDPSF  EQTTGNL...  LLDGFINGVG

TM2                         TM3
        ----------------            ----------------
               X               X
SEL-12  MLCVVVLMTV  LLIVFYKYKF  YKLIHGWLIV  SSFLLLF...  .......LFTT
  S182  MISVIVVMTI  LLVVLYKYRC  YKVIHAWLII  SSLLLLF...  .......FFSF
  E5-1  MISVIVVMTI  FLVVLYKYRC  YKFIHGWLIM  SSLMLLF...  .......LFTY
 SPE-4  TILVLGCVSF  IMLAFVLFDF  RRIVKAWLTL  SCLLILFGVS  AQTLHDMFSQ

TM4
        ---           ----------------------
SEL-12  IYVQEVLKSF  DVSPSALLVL  FGLGNYGVLG  MMCIHWKGPL  RLQQFYLITM
  S182  IYLGEVFKTY  NVAVDYVTVA  LLIWNFGVVG  MISIHWKGPL  RLQQAYLIMI
  E5-1  IYLGEVLKTY  NVAMDYPTLL  LTVWNFGAVG  MVCIHWKGPL  VLQQAYLIMI
 SPE-4  VFDQDDNNQY  YMTIVLIVVP  TVVYGFG..G  IYAFFSNSSL  ILHQIFVVTN

TM5             TM6
        ----------    ----------------------
         X                       X               X
SEL-12  SALMALVFIK  YLPEWTVWFV  LFVISVWDLV  AVLTPKGPLR  YLVETAQERN
  S182  SALMALVFIK  YLPEWTAWLI  LAVISVYDLV  AVLCPKGPLR  MLVETAQERN
  E5-1  SALMALVFIK  YLPEWSAWVI  LGAISVYDLV  AVLCPKGPLR  MLVETAQERN
 SPE-4  CSLISVFYLR  VFPSKTTWFV  LWIVLFWDLF  AVLAPMGPLK  KVQEKASDYS
```

FIGURE 2B

```
                        TM7
            -----------------------
                XX
SEL-12   EPIFPALIYS SGVIYPYVLV TAVENTTDPR EPTSSDSNTS TAFPGEASCS
  S182   ETLFPALIYS STMVW...LV NMAEGDPEAQ RRVSKNSKYN AESTERESQD
  E5-1   EPIFPALIYS SAMVW...TV GMAKLDP... ...SSQGALQ LPYDPEMEED
 SPE-4   KCVLNLIMFS ANEKRLTAGS NQEETNEGEE STIRRTVKQT IEYYTKREAQ

SEL-12   SE........ .......... .......... ..TPKRPKVK RIPQKVQIES
  S182   T......... .......... .......... ........VA ENDDGGFSEE
  E5-1   S......... .......... .......... ........YD SFGEPSYPEV
 SPE-4   DDEFYQKIRQ RRAAINPDSV PTEHSPLVEA EPSPIELKEK NSTEELSDDE

SEL-12   NTTASTTQNS GVRVERELAA ERPTVQDANF HRHEEEERG. ..........
  S182   WEAQRDSHLG PHRSTPESRA AVQELSSSIL AGEDPEERG. ..........
  E5-1   FEPPLTGYPG EEL....... .......... ..EEEERG.  ..........
 SPE-4   SDTSETSSGS SNLSSSDSST TVSTSDISTA EECDQKEWDD LVSNSLPNND

X              X
                                                        ---------
SEL-12   .......... .....VKLGL GDFIFYSVLL GKASSYF..D WNTTIACYVA
  S182   .......... .....VKLGL GDFIFYSVLV GKASATASGD WNTTIACFVA
  E5-1   .......... .....VKLGL GDFIFYSVLV GKAAATGSGD WNTTLACFVA
 SPE-4   KRPATAADAL NDGEVLRLGF GDFVFYSLLI GQAAASGCP. .FAVISAALG

TM8
         ---------------
SEL-12   ILIGLCFTLV LLAVFKRALP ALQFPFSPDS FTTFVPAGSS PHLLHKSLKS
  S182   ILIGLCLTLL LLAIFKKALP ALPISITFGL VFYFATDYLV QPFMDQLAFH
  E5-1   ILIGLCLTLL LLAVFKKALP ALPISTTFGL IFYFSTDNLV RPFMDTLASH
 SPE-4   ILFGLVVTLT VFSTEESTTP ALPLPVICGT FCYFSSMFFW EQLYG.....

TM9?
         ---------------
SEL-12   VYYINSLFLP FLCIINFSII S
  S182   QFYI...... ..........  
  E5-1   QLYI...... ..........  
```

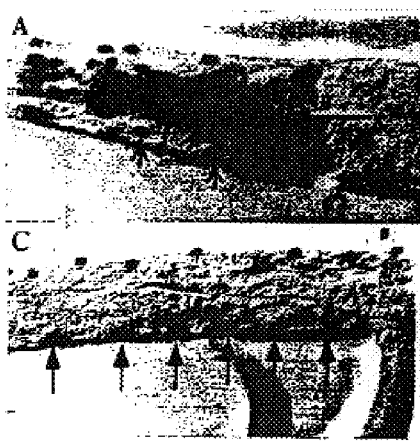
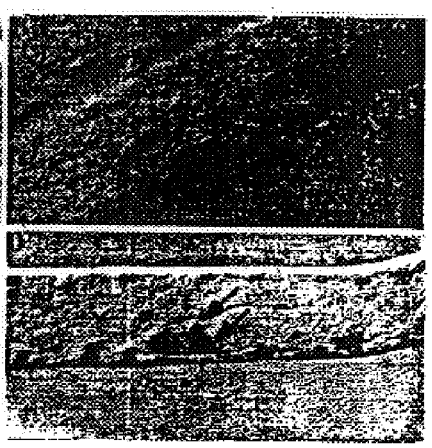
FIGURE 3A  FIGURE 3B
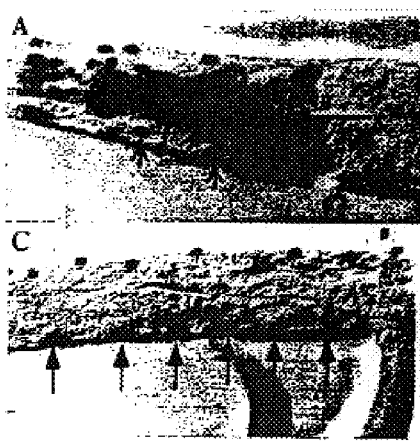
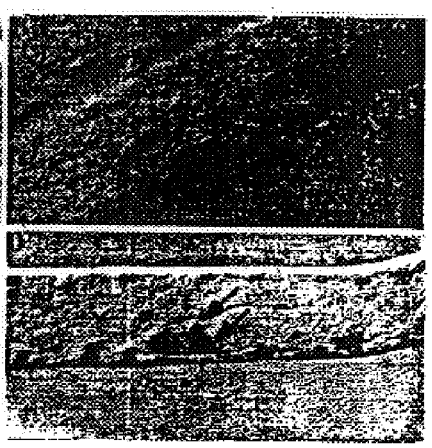
FIGURE 3C  FIGURE 3D

IDENTIFICATION OF SEL-12 AND USES THEREOF

This application claims benefit of U.S. Provisional Application No. 60/004,387, filed Sep. 27, 1995, the content of which is incorporated into this application by reference. Within this application, publications are referenced within parentheses. Full citations for these references may be found at the end of each series of experiments. The disclosures of these publications in their entireties are hereby incorporated by reference into this application in order to more fully describe the state of the art to which this invention pertains.

BACKGROUND OF THE INVENTION

The lin-12 gene of *C. elegans* is the archetype of the, "lin-12/Notch" gene family found throughout the animal kingdom (reviewed in Greenwald and Rubin, 1992). Members of this family appear to function as receptors for intercellular signals that specify cell fates during development. Essentially, lin-12 activity controls binary decisions: if a cell has a choice between two fates, A and B, activation of lin-12 above a threshold value causes the cell to adopt fate A, whereas the failure to activate lin-12 above the threshold causes the cell to adopt fate B (Greenwald et al. 1983). Furthermore, inappropriate activation of mammalian lin-12/Notch genes have been implicated in oncogenesis (Ellisen et al., 1991; Robbins et al., 1993) and in normal development (e.g. Swiatek et al., 1993). Much of the work in applicants, laboratory is focused on understanding how lin-12 specifies cell fates. An important component of this endeavor is the identification of genes that influence lin-12 activity and the identification of potential "downstream" genes.

Applicants identified the sel-12 gene by screening for suppressors of the "Multivulva" phenotype caused by an allele of lin-12 that causes constitutive LIN-12 activation. Applicants performed a genetic and molecular characterization of sel-12, which established: (1) Reducing or eliminating sel-12 activity reduces the activity of lin-12 and of glp-1, another member of the lin-22/Notch family. In addition, reducing or eliminating sel-12 activity causes and egg-laying defective (Egl) phenotype. Applicants do not know if the Egl phenotype is a direct consequence of reducing lin-12 activity or an independent effect of reducing sel-12 activity. (2) sel-12 and lin-12 can functionally interact within the same cell. (3) sel-12 is predicted to encode a protein with multiple transmembrane domains that is highly similar to S182, which has been implicated in early-onset familial Alzheimer's disease (Sherrington et al., 1995). These findings have been described in a paper that has been accepted by *Nature* (Levitan and Greenwald, 1995). In addition, applicants have data indicating that sel-12 is more broadly expressed than lin-12, including a lot of expression in neurons.

The remarkable conservation of the SEL-12 and S182 predicted protein structure suggests that their functions are likely to be conserved as well. Recently, a second gene known as E5-1 or STM2 has been implicated in early-onset familial Alzheimer's disease (Levy-Lahad et al, 1995; Rogaev et al, 1995) E5-1/STM2 encodes a protein that is highly similar to S182 (Levy-Lahad et al, 1995b; Rogaev et al, 1995) and SEL-12. Furthermore, it is striking that four of the five changes in S182 or E5-1/STM2 associated with early-onset familial Alzheimer's disease alter amino acids that are absolutely conserved in the worm and the human proteins, and that the tenth alters an amino acid that has been changed very conservatively during evolution. Applicants hope to bring the powerful tools of classical and molecular genetic studies in *C. elegans* to bear on fundamental issues of SEL-12/S182/E5-1 structure and function. Thus, far, proteins similar to LIN-12 and SEL-12 have not been described in single-celled organisms, so *C. elegans* may be the simplest practical system for studying these issues in vivo.

SUMMARY OF THE INVENTION

This invention provides an isolated nucleic acid molecule encoding a SEL-12 protein. This invention further provides an isolated nucleic acid molecule which encodes a mutated SEL-12 protein. This invention also provides an isolated nucleic acid molecule which encodes a mutated SEL-12, wherein the mutated SEL-12 contains at least one of the following: position 115 is a leucine, position 132 is an arginine, position 215 is a glutamic acid, position 229 is a valine, position 254 is a valine, position 255 is a valine, position 371 is a valine, position 387 is tyrosine, position 104 is an isoleucine or position 204 is a valine. This invention further provides different uses of these nucleic acid molecules. This invention also provides different sel-12 mutants and transgenic animals which carry wild-type or mutated sel-12.

Figure 1B:
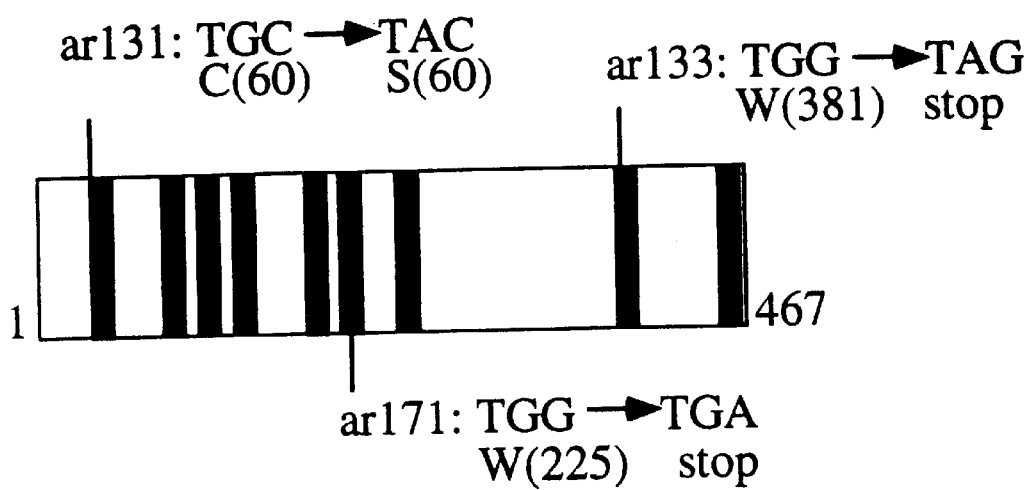
FIG. 1: A. Nucleotide sequence and the deduced amino acid sequence of the sel-12 cDNA. The first 22 nucleotides, shown in italics, correspond to the sequence of the trans-spliced leader SL1, a sequence found on the 5' end of many *C. elegans* transcripts 26. Potential membrane-spanning domains are underlined. No potential signal sequence was identified. Analysis of the amino acid sequence using the Kyte-Doolittle algorithm predicts that all nine domains have high enough hydrophobicity values to span a membrane. Three potential glycosylation sites (N-X-T/S) in the region between the seventh and eighth putative transmembrane domains are shown in italics at positions 273, 286, and 319 of the amino acid sequence. The locations of the introns are indicated by a caret over the nucleotide preceding the intron. sel-12 contains seven exons and six introns and spans 2.3 kb of genomic DNA.

B. Schematic representation of the SEL-12 protein and molecular lesions associated with three sel-12 alleles. Filled rectangles indicate nine hydrophobic regions. Based on the Kyte-Doolittle algorithm, they are potential membrane spanning domains. The fifth hydrophobic region contains only 18 amino acids and the sixth hydrophobic region contains a charged residue; however, these features are conserved in S182, so applicants infer that they are likely to be bona fide membrane-spanning domains. The ninth hydrophobic domain is not followed by a basic amino acid and is not conserved in S182 (although the C-terminus of S182 is relatively hydrophobic), so the inference that it is a membrane-spanning domain is more tentative. No potential signal sequence was identified.

FIG. 2: Predicted protein sequence of SEL-12 and its alignment with the predicted protein sequences of S182 and E5-1/STM2. The Pileup program of the GCG-Wisconsin package was used to create this alignment. Amino acids that are identical between SEL-12 and one or more of the other proteins are highlighted in black, and predicted transmembrane domains are overlined. S182 is the predicted protein of a gene associate with early-onset familial Alzheimer's disease (Sherrington et al., 1995). E5-STM2 has also been implicated in early-onset familial Alzheimer's disease (Levy-Lahad et al., 1995a,b; Rogaev et al., 1995). The positions of the ten mutations associated with disease in S182 and E5-1/STM2 (Levy-Lahad et al., 1995b; Rogaev et al., 1995; Sherrington et al., 1995) are indicated (X), and tabulated in Table 1 below. SEL-12 and S182 are 48% identical, SEL-12 and E5-1/STM2 are 51% identical, and S182 and E-51/STM2 are 67% identical (Levy-Lahad et al., 1995b; Rogaev et al., 1995). SPE-4 is the predicated protein of the spe-4 gene of C. elegans, which is required for spermatogenesis (L'Hernault and Arduengo, 1992). SEL-12, S182 and E5-1/STM2 appear to be much more closely related to each other than they are to SPE-4. For example, S182 and SPE-4 are only 22% identical, with several large gaps. Furthermore, several regions that are very highly conserved between SEL-12, S182 and E5-1/STM2 are not conserved in SPE-4, and only one of the ten mutations associated with Alzheimer,s disease affects an amino acid that is identical in SPE-4.

FIG. 3. Transgenic hermaphrodites expressing a sel-12::lacZ transgene. Expression is seen in neural and non-neural cells. A. Adult. Large arrow indicates nerve ring; smaller arrows indicate muscle nuclei. B. Adult. Arrows indicate ventral cord nuclei. C. L3 larva. Arrows indicate nuclei of the vulval precursor cells P3.p–P8.p. D. L2 larva. Arrows indicate the nuclei of the somatic gonadal cells Z1.ppp and Z4.aaa. sel-12 activity has been shown to influence the fates of P3.p–P8.p, and Z1.ppp and Z4.aaa in sensitized genetic backgrounds (11 of the Third Series of Experiments). Compromised neural function associated with reduced activity has not yet been seen in the nerve ring or ventral cord, possibly because an appropriate sensitized genetic background has not been examined. Complete genotype: smg-1(r861) unc-54(r293); arIs17 [pRF4, pIB1Z17].

DETAILED DESCRIPTION OF THE INVENTION

This invention provides an isolated nucleic acid molecule encoding a SEL-12. This invention further provides an isolated nucleic acid molecule which encodes a mutated SEL-12. This invention also provides an isolated nucleic acid molecule which encodes a mutated SEL-12, wherein the mutated SEL-12 contains at least one of the following: position 115 is a leucine, position 132 is an arginine, position 215 is a glutamic acid, position 229 is a valine, position 254 is a valine, position 255 is a valine, position 371 is a valine, position 387 is tyrosine, position 104 is an isoleucine or position 204 is a valine. In an embodiment, the mutation is generated by in vitro mutagenesis.

In an embodiment, the isolated nucleic acid molecule is a DNA molecule. In a further embodiment, the DNA is a cDNA molecule. In another further embodiment, the DNA is a genomic DNA molecule. In a separate embodiment, the nucleic acid molecule is an isolated RNA molecule.

This invention also provides the above nucleic acid molecule which encodes substantially the same amino acid sequence as shown in FIG. 1A.

This invention also provides a nucleic acid molecule of at least 15 nucleotide capable of specifically hybridizing with a unique sequence within the sequence of a nucleic acid molecule described above. In an embodiment, these nucleotide are DNA. In another embodiment, these nucleotide are RNA.

This invention also provides a vector which comprises the above-described isolated nucleic acid molecule. This invention also provides the above-described isolated nucleic acid molecules operatively linked to a promoter of RNA transcription.

In an embodiment, the vector is a plasmid. In an embodiment, the Sel-12 genomic DNA, a MunI/XhoI genomic fragment was cloned into the Bluescript KS$^+$ plasmid which was cut with EcoRI and XhoI. The resulting plasmid is designated as PMXB.

The plasmids designated pMX8 and p1-1E were deposited on Sep. 14, 1995, pursuant to the requirements of the Budapest Treaty on the International Recognition of the Deposit of Microorganisms for the Purposes of Patent Procedure with the American Type Culture Collection (ATCC), 10801 University Boulevard, Manassas, Va. 20110-2209, under ATCC Designation Nos. 97278, and 97279, respectively. During the pendency of the subject application, access to the deposit shall be afforded to the Commissioner upon request. All restrictions upon public access to this deposit shall be removed upon the grant of a patent on this application and the deposits shall be replaced if viable samples cannot be made by the depository named hereinabove.

This plasmid, pMX8 was deposited with the American Type Culture Collection (ATCC), 12301 Parklawn Drive, Rockville, Md. 20852, U.S.A. on Sep. 14, 1995 under the provisions of the Budapest Treaty for the International Recognition of the Deposit of Microorganism for the Purposes of Patent Procedure. The pMX8 was accorded with ATCC Accession number 97278.

In another embodiment, a Sel-12 cDNA, an EcoRI cDNA fragment was cloned into the Bluescript KS$^+$ plasmid which is cut with EcoRI. The resulting plasmid is designated p1-1E. The plasmid, p1-1E was deposited with the American Type Culture Collection (ATCC), 12301 Parklawn Drive, Rockville, Md. 20852, U.S.A. on Sep. 14, 1995 under the provisions of the Budapest Treaty for the International Recognition of the Deposit of Microorganism for the Purposes of Patent Procedure. The p1-1E was accorded with ATCC Accession number 97279. This plasmid p1-1E containing a frameshift mutation in the 3' end of the coding region of the cDNA. It can be easily corrected to the wild-type sequence as the complete sequence of Caenorhabditis elegans has been known.

This invention also provides a host vector system for the production of a polypeptide having the biological activity of a SEL-12 or a mutated SEL-12 which comprises the above-described vector and a suitable host. The suitable hosts include but are not limited to bacterial cells, insect cells, plant and mammalian cells.

This invention also provides purified SEL-12 and mutated SEL-12.

This invention also provides a purified SEL-12 protein or a purified SEL-12 fragment thereof. This invention further provides a purified mutated SEL-12 protein or a purified mutated SEL-12 fragment thereof.

This invention provides a method for production of an antibody capable of binding to wild-type and/or mutant S182 or E5-1/STM2 comprising: a) administering an amount of the purified protein or fragment of SEL-12 or mutated SEL-12 to a suitable animal effective to produce an antibody against SEL-12 or mutated SEL-12 protein in the animal; and b) testing the produced antibody for capability to bind wild-type and/or mutant S182 or E5-1/STM2.

In an embodiment, the antibody is produced by in vitro immunization. In another embodiment, the antibody is produced by screening a differential phage display library. The produced antibody may be tested by Western blot analysis, immunoprecipitation, staining of cells or tissue sections or in combination of the above.

This invention also provides a method for production of an antibody capable of binding to wild-type and/or mutant S182 or E5-1/STM2 comprising: a) determining conserved regions revealed by alignment of the SEL-12, S182 and E5-1/STM2 protein sequences; b) synthesizing peptides corresponding to the revealed conserved regions; c) administering an amount of the synthesized peptides to a suitable animal effective to produce an antibody against the peptides in the animal; and b) testing the produced antibody for capability to bind wild-type and/or mutant S182 or E5-1/STM2.

In an embodiment, the antibody is produced by in vitro immunization. In another embodiment, the antibody is produced by screening a differential phage display library. The produced antibody may be tested by Western blot analysis, immunoprecipitation, staining of cells or tissue sections or in combination of the above.

This invention provides antibodies produced by above methods. This invention intends to cover other methods of production of antibodies capable of binding to wild-type and/or mutant S182 or E5-1/STM2 using the SEL-12 protein or sel-12. This invention also provides monoclonal antibodies capable of binding to wild-type and/or mutant S182 or E5-1/STM2.

This invention also provides antibodies capable of specifically recognizing SEL-12 protein or mutated SEL-12 protein. As used herein the term "specifically recognizing" means that the antibodies are capable of distinguish SEL-12 protein or mutated SEL-12 proteins from other proteins.

This invention also provides transgenic animals which express the above nucleic acid molecules. In an embodiment, the animal is a Caenorhabditis elegans. This invention also provides transgenic Caenorhabditis elegans animals comprising wild-type or mutant human S182 gene. This invention further provides transgenic Caenorhabditis elegans animals comprising wild-type or mutant human STM2/E5-1 gene.

This invention provides the above transgenic Caenorhabditis elegans animals, wherein the wild-type or mutant human S182, or wild-type or mutant STM2/E5-1 gene is under the control of sel-12 or lin-12 regulatory sequence.

This invention also provides a method for identifying a compound which is capable of ameliorating Alzheimer disease comprising administering effective amount of the compound to the transgenic animals or sel-12 mutants, the alteration of the conditions of the transgenic animal indicating the compound is capable of ameliorating Alzheimer disease.

This invention also provides a previously unknown compound identified by the above method. This invention provides a pharmaceutical composition comprising an effective amount of the compound identified by the above method and a pharmaceutically acceptable carrier.

Pharmaceutically acceptable carriers are well known to those skilled in the art. Such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention further provides a method for determining whether a compound might be capable of ameliorating Alzheimer's disease comprising: a) treating Caenorhabditis elegans mutants having reduced, increased or altered sel-12 activity with the compound; and b) determining whether the compound suppresses, enhances or has no effect on the phenotype of the mutant, the suppression or enhancement of the phenotype indicating the compound is capable of ameliorating Alzheimer's disease.

This invention provides a pharmaceutical composition comprising an effective amount of the compound determined by the above method to be capable of ameliorating Alzheimer's disease and a pharmaceutically acceptable carrier.

This invention provides a method for identifying a suppressor of the multivulva phenotype of lin-12 gain-of-function mutation comprising: a) mutagenizing lin-12 Caenorhabditis elegans worms with an effective amount of an appropriate mutagen; b) screening for revertants in the F1, F2 and F3 generations; and c) isolating the screened revertant, thereby identifying a suppressor of the multivulva phenotype of lin-12. This invention also provides suppressors identified by the above method.

In an embodiment, this invention provides a Caenorhabditis elegans animal having a suppressor, designated sel-12 (ar131). This nematode was deposited with the American Type Culture Collection (ATCC), 12301 Parklawn Drive, Rockville, Md. 20852, U.S.A. on Sep. 27, 1995 under the provisions of the Budapest Treaty for the International Recognition of the Deposit of Microorganism for the Purposes of Patent Procedure. sel-12(ar131) was accorded with ATCC Accession number 97293. In another embodiment, this invention provides an animal having a suppressor designated sel-12(ar133).

This invention also provides a method for identifying a mutant sel-12 gene which reduces sel-12 function comprising: a) mutagenizing Caenorhabditis elegans worms with an effective amount of an appropriate mutagen; b) performing complementation screening of the mutagenized worms to determine if a descendant of a mutagenized worm bears a mutation that fails to complement one of the above-described suppressor for the Egl defect; and c) isolating the individual worm and determining the phenotype of worms carrying the new allele in its homozygous form and in trans to a deficiency, thereby identifying a mutant sel-12 gene which reduces sel-12 function. In an embodiment, this invention provides the above method which further comprises performing DNA sequence analysis of the identified mutant sel-12 gene to determine the molecular lesion responsible for the mutation.

This invention also provides mutant sel-12 genes identified by the above methods. In an embodiment, this invention provides an animal having a mutant sel-12 gene, designated sel-12 (ar171). This nematode was deposited with the American Type Culture Collection (ATCC), 12301 Parklawn Drive, Rockville, Md. 20852, U.S.A. on Sep. 27, 1995 under the provisions of the Budapest Treaty for the International Recognition of the Deposit of Microorganism for the Purposes of Patent Procedure. sel-12(ar171) was accorded with ATCC Accession number 97292.

This invention provides a method for producing extragenic suppressors of a sel-12 allele comprising: a) mutagenizing sel-12 mutant hermaphrodites with an effective amount of a mutagen; b) screening for revertants in the F1, F2 and F3 generations; and c) isolating the screened revertant.

This invention also provides a method for producing extragenic suppressors of a sel-12(Alz) mutant comprising: a) mutagenizing sel-12 (Alz) hermaphrodites with an effective amount of a mutagen; b) screening for revertants in the F1, F2 and F3 generations; and c) isolating the screened revertant.

Appropriate mutagens which may be used in this invention are well known in the art. In an embodiment, the mutagen is ethyl methanesulfonate.

This invention also provides suppressors produced by the above methods. This invention further provides a method for identification of a suppressor gene comprising performing DNA sequence analysis of the above suppressors to identify the suppressor gene. This invention also provides the identified suppressor gene by the above method.

This invention will be better understood from the examples which follow. However, one skilled in the art will readily appreciate that the specific methods and results discussed are merely illustrative of the invention as described more fully in the claims which follow thereafter.

Experimental Details

First Series of Experiments

Materials and Methods

Applicants genetically mapped sel-12 to the left of unc-1 X: from hermaphrodites of genotype sel-12(ar131) dpy-3 (e27)/unc-1(e538), 1/36 Sel non-Dpy and 18/19 Dpy non-Sel recombinants segregated unc-1. To clone se1-12, applicants used the well correlated genetic and physical maps in the sel-12 region to identify cosmid clones that potentially carried the sel-12 gene (ref. 27 and A. Coulson et al., personal communication). Applicants assayed pools and single cosmids for the ability to rescue the Egl defect of sel-12 (ar131) hermaphrodites, using the plasmid pRF4 [rol-6 (su1006)] as a dominant cotransformation marker (28). Ultimately, applicants found that pSpX4, containing a 3.5 kb_SpeI/+XhoI subclone of C08A12 (Subcloned into KS Bluescript, Stratagene) completely rescue sel-12(ar131). When this subclone was microinjected at a concentration of 10 µg/ml into sel-12(ar131) animals, 6/6 lines all demonstrated rescue of the Egl phenotype. When applicants attempted to obtain transgenic lines carrying pSpX4 using a concentration of 50 µg/ml, applicants obtained F1 transformants but no stable lines perhaps indicating some toxicity of this plasmid at higher concentrations. Applicants used this genomic subclone to screen a cDNA library and identified one class of clones of 1.5 kb in size. All subcloning, restriction digests, and library screening were done according to standard techniques (29). Applicants sequenced both strands of the cDNA clone after generating systematic deletions using the Erase-a-base system (Promega®). DNA sequence was performed on double stranded templates using Sequenase™ (US Biochemical). The cDNA contained both a poly (A) tail and a portion of the spliced leader sequence SL1 (ref. 30), suggesting it was a full length clone. Applicants confirmed the 5' end of the cDNA by reverse transcription followed by polymerase chain reaction (RT-PCR) (31). The sequence of this full-length cDNA can be found through GenBank under accession number U35660.

To identify the lesions associated with sel-12 alleles applicants used PCR to amplify the sel-12 genomic fragment from DNA isolated from the sel-12 mutant strains using the primers DL103 (5' TGTCTGAGTTACTAGTTTTCC 3') (SEQ. ID. NO:7) and DLG3 (5' GGAATCTGAAGCACCT-GTAAGCAT 3') (SEQ. ID. NO:8). An aliquot of this double-stranded amplification product was used as the template in a subsequent round of PCR using only the primer DL103, to generate a single-stranded template. Exon specific primers were used to determine the entire coding sequence for all three alleles. For each allele, only one alteration in sequence was identified.

Experimental Result and Discussion

The lin-12(d) hypermorphic mutation lin-12(n950) causes a Multivulva phenotype characterized by the production of ectopic pseudovulvae (3, 4). Applicants screened for non-Multivulva revertants after ethyl methanesulfonate mutagenesis (5) of lin-12(n950) hermaphrodites; two recessive suppressors, ar132 and ar133, proved to be alleles of a new gene, sel-12 (sel means suppressor and/or enhancer of lin-12). These sel-12 alleles cause an incompletely penetrant, recessive egg-laying defective (Egl) phenotype in a lin-12(+) background. Since sel-12(ar131) is viable, fertile and Egl in trans to a deficiency (data not shown), applicants also performed a screen for mutations that fail to complement the Egl defect of sel-12(ar131). From a screen of 5900 mutagenized haploid genomes, applicants identified two additional sel-12 alleles. One allele obtained in this screen, sel-12(ar171), displays a completely penetrant Egl defect as a homozygote and in trans to a deficiency, suggesting that sel-12(ar171) strongly reduces sel-12 function. This inference is supported by the molecular analysis described below, which revealed that the ar171 lesion would result in a truncated protein product.

The Egl phenotype caused by sel-12 mutations in a lin-12(+) background is reminiscent of the Egl phenotype caused by reducing lin-12 activity (see Table 1 legend). However, a more general involvement of sel-12 in lin-12- and glp-1-mediated cell fate decisions becomes apparent when the phenotypes of lin-12; sel-12 and glp-1; sel-12 double mutants are analyzed (Table 1). Applicants examined the genetic interactions of sel-12 with two lin-12 hypomorphic mutations, with a lin-12(d) hypermorphic mutation, and with a glp-1 hypomorphic mutation. In all cases, applicants found that reducing sel-12 activity reduces lin-22 or glp-1 activity. These genetic interactions are exemplified by the effects of sel-12 on two lin-12-mediated decisions, the anchor cell/ventral uterine precursor cell (AC/VU) decision and vulval precursor cell (VPC) specification.

The AC/VU decision involves an interaction between two initially equivalent cells of the somatic gonad, Z1.ppp and Z4.aaa. In a given hermaphrodite, Z1.ppp and Z4.aaa interact so that one of these cells becomes the AC while the other becomes a VU (6, 7, 8). When lin-12 activity is eliminated, both Z1.ppp and Z4.aaa become ACs (the "2 AC defect"), and when LIN-12 is activated, as in lin-12(d) mutants, both Z1.ppp and Z4.aaa become VUs (the "0 AC defect") (3,9). Two observations indicate that sel-12 reduces lin-12 activity in Z1.ppp and Z4.aaa. First, sel-12 dramatically enhances the penetrance of the 2 AC defect of lin-12 hypomorphs (Table 1A). For example, 30% of lin-12 (n676n930) hermaphrodites have 2 AC (10), whereas essentially all lin-12 (n676n930); sel-12(ar171) have 2 ACs. Second, sel-12 partially suppresses the 0 AC defect caused by LIN-12 activation (Table 1B). For example, all lin-12(n950) hermaphrodites lack an AC, whereas 10% of lin-12(n950); sel-12(ar171) hermaphrodites have an AC.

TABLE 1 sel-12(ar171) reduces lin-12 and glp-1 activity

| Genotype | % 2ACs | % ventral coelomocytes | fertility | % L1 arrest[k] |
|---|---|---|---|---|
| A. Enhancement of hypomorphic lin-12 alleles by sel-12 (ar171) | | | | |
| wild type[a] | 0 | 0 | yes | 0 |
| sel-12(ar171)[b] | 0 | 0 (0/17) | yes | 0 (n = 233) |
| lin-12 (n676n930)[c] | 30 g | 8 (1/12) | yes | 9 (n = 233) |
| lin-12 (n676n930); sel-12(ar171)[d] | 95 (n = 41) | 92 (12/13) | no | 17 (n = 177) |
| lin-12(ar170)[e] | 16 (n = 32) | 0 (0/32) | yes | 0 (n = 209)[i] |
| lin-12(ar170); sel-12(ar171)[f] | 98 (n = 47) | 0 (0/47) | yes | 0 (n = 111) |
| lin-12(0) | 100[h] | 100[h] | no | 10[j] |

| Genotype | number of VPCs adopting a vulval fate/ hermaphrodite | % 0 AC |
|---|---|---|
| B. Suppression of a hypermorphic lin-12 allele by sel-12(ar171) | | |
| wild type[a] | 3 | 0 |
| lin-12(n950)[l] | 6 (n = 7) | 100 |
| sel-12(ar171)[b] | 3 (n = 10) | 0 (n = 108) |
| lin-12(n950); sel-12(ar171)[m] | 2–4 (n = 8) | 89.5 (n = 57) |

| Genotype | % sterility in both gonad arms | % sterility in one gonad arm |
|---|---|---|
| C. Enhancement of glp-1(e2141) by sel-12(ar171) | | |
| wild type[a] | 0 | 0 |
| glp-1(e2141)[n] | 8.5 (n = 259) | 4.0 (n = 259) |
| sel-12(ar171)[b] | 0 | 0 |
| glp-1(e2141); sel-12(ar17)[o] | 25 (n = 422) | 8.8 (n = 422) |

[a] *C. elegans* var. Bristol strain N2
[b] sel-12(ar171) unc-1(e538)
[c] lin-12(n676n930); unc-1(e538)
[d] lin-12(n676n930); sel-12(ar171) unc-1(e538)
[e] lin-12(ar170); unc-1(e538)
[f] lin-12(ar170); sel-12(ar171) unc-1(538)
[g] see ref. 10
[h] lin-12(n137n720); see ref. 3
[i] lin-12(ar170) [not unc-1]
[j] lin-12(n941) see ref. 23
[k] some L1 arrested animals were examined for Lag phenotypes, i.e. lack of an anus and rectum, lack of an excretory cell and a twisted nose. These phenotypes were observed for all genotypes where L1 arrested animals were identified.
[l] lin-22(n950); unc-1(e538)
[m] lin-12(n950); sel-12(ar171) unc-1(e538)
[n] glp-1(e2141); unc-1(e538)
[o] glp-1(e2141; sel-12(ar171) unc-1(e538)

Table 1. Legend

Most lin-12- and glp-1-mediated cell fate decisions appear normal in sel-12(ar171) mutants. However, the egg-laying defect of sel-12(ar171) hermaphrodites resembles the egg-laying defect of lin-12 hypomorphic mutants (10): sel-12(ar131) hermaphrodites leak occasional eggs and larvae, and like lin-12 hypomorphic mutants, sel-12 mutants have morphologically normal HSNs, sex muscles and VPC lineages. Egg-laying is particularly sensitive to reduction in lin-12 activity (10); H. Wilkinson and I. G., unpublished observations). It is therefore possible that both lin-12 and sel-12 are required for an as yet unidentified cell fate decisions) underlying the egg-laying defect. The fact that sel-12(ar171) mutants do not display all of the defects associated with loss of lin-12 function may indicate that sel-12(ar171) is not a null allele or sel-12 function is partially redundant with the function of another gene.

A. Cell fate transformations were scored at 25° using criteria described in (3) unless otherwise indicated. At 25° lin-12(n676n930) behaves like a hypomorph, whereas at 15° C., lin-12(n676n930) has mildly elevated lin-12 activity (10). Since lin-12(n676n930); sel-12(ar171) hermaphrodites are sterile at 25° C., applicants shifted fertile lin-12(n676n930); sel-12 (ar171) hermaphrodites from 15° C. to 25° C. so that their progeny could be scored for cell fate transformations and other defects. lin-12(ar170) behaves like a hypomorph for the,AC/VU decision (J. Hubbard and I. G., unpublished observations). In strains containing lin-12(ar170), cell fate transformations were scored in hermaphrodites raised at 20°; other defects were scored in the progeny of hermaphrodites grown at 20° and shifted to 25°.

% 2ACs: In lin-12(0) mutants, both Z1.ppp and Z4.aaa become ACs, so lin-12(0) hermaphrodites have two ACs; in lin-12(d) mutants such as lin-12(n950), both Z1.ppp and Z4.aaa become VUs, so lin-12(d) hermaphrodites have 0 ACs. The number of anchor cells was scored in the L3 stage using Nomarski microscopy. For all genotypes, hermaphrodites either had one or two ACs.

ventral coelomocytes: The fates of two pairs of cells, M.d(l/r)pa and M.v(l/r)pa are affected by mutations in lin-12. In wild type, the ventral pair of cells gives rise to one sex-myoblast and one body muscle; the dorsal pair gives rise to coelomocytes. In lin-12(0) animals, the ventral pair as well as the dorsal pair gives rise to coelomocytes, so that lin-12(0) hermaphrodites have extra ventral coelomocytes; in lin-12(d) animals, both pairs of cells give rise to sex myoblasts/body muscles. The presence of ventral coelomocytes was scored in the L3 stage. For all genotypes, the absence of ventral coelomocytes suggests that the sex myoblast was specified normally (see ref. 3).

Fertility: fertility was scored by the appearance of eggs either on the plate or inside the hermaphrodite and the ability to propagate the strain.

L1 arrest: Full viability requires activity of lin-12 or a related gene, glp-1. lin-12(0) glp-1(o) double mutants display a fully penetrant L1 arrest phenotype and a Lag phenotype characterized by specific cell fate transformations (23). lin-12(0) single mutants display a low penetrance L1 arrest phenotype and a somewhat lower penetrance Lag phenotype (23). Single gravid hermaphrodites were placed on a plate at 25° C. Most of the hermaphrodites were completely egg-laying defective and laid no eggs; some lin-12(n676n930) animals released a few eggs or larvae before turning into "bags of worms", in which case the hermaphrodite was transferred after a day. Since lin-12(n676n930) animals can grow slowly at 25° C., L1 arrested animals were scored three days after all the eggs had hatched. Arrested L1 animals were spot-checked for the presence of Lag phenotypes using Nomarski microscopy. Some arrested L1 animals of each genotype displayed Lag phenotypes (data not shown).

B. Animals were grown at 20°C. VPC fates were scored by determining the cell lineages of P3.p–PB.p in each animal (Table 2 and data not shown). The number of ACs were scored as described above. For all genotypes, hermaphrodites had either zero or one AC.

C. glp-1(e2141ts) is weakly hypomorphic at 20 and essentially wild-type at 15° (24). Strains containing glp-1(e2141) were maintained at 15°; fertile adults grown at 15° were placed at 20°, and their progeny grown at 20° were scored for sterility. Other strains were maintained continuously at 20°. glp-1 activity controls the decision of germline nuclei between mitosis and meiosis (25, 24); L. W. Berry and T. Schedl, personal communication). GLP-1 is thought to be the receptor for the inductive signal from the distal tip cells of the somatic gonad that promotes germline mitosis (and/or inhibits meiosis) (7). When glp-1 activity is eliminated, germline nuclei enter meiosis (25). Hermaphrodites of each genotype were scored for sterility in one or both gonad arms in the dissecting microscope. Several sterile or half-sterile individuals were examined by Nomarski microscopy, and sterile gonad arms were found to have the characteristic Glp phenotype (data not shown).

Each of the six VPCs, P3.p–P8.p, has the potential to adopt one of two vulval fates, termed "1°" and "2°", or a non-vulval fate, termed "3°" (11, 12). Normally, P5.p, P6.p, and P7.p adopt vulval fates, in a 2°-1°-2° pattern (13). This pattern is the outcome of the integration of two signalling inputs: a let-60 Ras-mediated inductive signal from the AC induces vulval fates, and a lin-12-mediated lateral signal between VPCs prevents adjacent VPCs from adopting the 1° fate (reviewed in ref. 14). The let-60 Ras-mediated inductive signal may cause expression or activation of the lateral signal (15, 16), which activates LIN-12 to cause a VPC to adopt the 2° fate (3, 17, 18).

Reducing sel-12 activity reduces lin-12 activity in lateral signalling that specifies the 2° fate of VPCs. First, sel-12 reduces the effect of activated LIN-12 in the VPCs: all VPCs adopt the 2° fate in lin-12(n950) hermaphrodites, but only half of the VPCs adopt the 2° fate in lin-12(n950); sel-12 (ar171) hermaphrodites (Table 1b, Table 2). Second, sel-12 reduces lateral signalling that occurs upon activation of let-60 Ras. Applicants analyzed VPC lineages (data not shown) in let-60(n1046) hermaphrodites, in which Ras has been activated by a codon 13 mutation (19, 20), and in let-60(n1046); sel-12(ar171) hermaphrodites. Lateral signalling appears to occur normally in let-60(n1046) hermaphrodites, since adjacent VPCs do not adopt the 1° fate (0/20 pairs of induced VPCs). In contrast, adjacent VPCs sometimes adopt the 1° fate in let-60(n1046); sel-12 (ar171) hermaphrodites (4/18 pairs), implying that reducing the activity of sel-12 reduces lateral signalling. Finally, some VPCs adopt the 2° fate in lin-12(n676n930) hermaphrodites (10). In contrast, VPCs do not adopt the 2° fate in lin-12 (n676n930); sel-12(ar171) double mutants (data not shown), although applicants have not tested whether this effect is due to the presence of a second AC.

TABLE 2 sel-12(ar171) plays a role in the receiving cells

| Genotype | Expression of 2° fate/total | | | | | | % VPCs adopting a 2° fate hermaphrodite |
|---|---|---|---|---|---|---|---|
| | P3.p | P4.p | P5.p | P6.p | P7.p | P8.p | |
| lin-12(n950) | 7/7 | 7/7 | 7/7 | 7/7 | 7/7 | 7/7 | 100 |
| lin-12(n950); sel-12(ar171) | 0/8 | 1/8 | 4/8* | 8/8 | 6/8 | 2/8** | 52 |
| lin-12(n-950) | X | 11/11 | X | X | X | X | 100 |
| lin-12(n950); sel-12(ar171) | X | 3/10 | X | X | X | X | 30 |

Table 2. Legend

X=cell killed by a laser microbeam. Numbers in each column correspond to the proportion of times a given VPC was observed to adopt the 2° fate (criteria as in ref. 18). All VPCs that did not undergo 2° fates underwent 3°, or non-vulval fates, with three exceptions: *=in 1/8 animals examined, P5.p underwent a hybrid (2°/3°) lineage; **=in 2/8 animals examined, P8.p underwent a hybrid (2°/3°) lineage. Animals were maintained at 20° C. Early L2 hermaphrodites (as judged by the size of the gonad) were chosen for laser ablation studies. The fates of the VPCs have not been determined at this time; the VPCs become determined many hours later, in the L3 stage (Sternberg and Horvitz, 1986). P3.p, and P5.p–P8.p were destroyed with a laser microbeam; the success of this operation was verified 2–3 hours later. The following day, the operated animals were mounted for Nomarski microscopy so that the cell lineage of P4.p could be observed directly. In both operated and unoperated animals, vulval fates were scored by directly observing the cell lineage of each VPC. The operated animals were observed until the early L4 stage, to ensure that no divisions were missed.

The genetic interactions of sel-12 with lin-12 imply a function for sel-12 in signalling and/or receiving cells during lateral specification. Applicants have tested whether sel-12 functions in the receiving end of lin-12-mediated cell-cell interactions by performing cell ablation experiments (Table 2). Applicants reasoned that, if all VPCs but one were ablated with a laser microbeam, the fate of the isolated VPC would reflect its intrinsic level of lin-12 activity in the absence of lateral signal. Thus, in lin-12(n950) hermaphrodites, an isolated VPC adopts the 2° fate (Table 2), suggesting that it has a high level of ligand-independent activation of LIN-12 in the VPCs (9). If sel-12 were to function in one VPC to lower lin-12 activity in another, then in lin-12(n950); sel-12(ar171) hermaphrodites, an isolated VPC should also adopt the 2° fate. However, if sel-12 were to function within a VPC to lower its lin-12 activity, then in lin-12(n950); sel-12(ar171) hermaphrodites, an isolated VPC should instead adopt the 3° fate. Applicants observed that in lin-12(n950); sel-12(ar171) hermaphrodites, an isolated P4.p often adopts the 3° fate (Table 2), implying that sel-12 functions within a VPC to lower lin-12 activity.

Applicants cloned sel-12 by transformation rescue (FIG. 1 legend), and determined the nucleotide sequence of a full-length cDNA (Genbank Accession number U35660). The predicted SEL-12 protein contains multiple potential transmembrane domains (FIG. 1B), consistent with SEL-12 function as a receptor, ligand, channel, or membrane structural protein. The SEL-12 protein is evolutionarily conserved. Database searches revealed a high degree of similarity to a sequence of a partial cDNA from human brain present on clone T03796 and a low degree of similarity to SPE-4, a protein required for C. elegans spermatogenesis (21). In addition, SEL-12 is highly similar to S182, which, when mutant, has been implicated in familial early-onset Alzheimer's Disease (22). T03796 has recently been shown to correspond to the E5-1/STM2 gene, which has also been S implicated in early onset familial Alzheimer's disease (Levy-Lahad et al., 1995a,b; Rogaev et al., 1995). The predicted protein sequences of SEL-12, E5-1/STM2, SPE-4, and S182 are aligned in FIG. 2.

lin-12/Notch genes specify many different cell fate decisions in C. elegans and Drosophila, and in both organisms some of these decisions are critical for neurogenesis. The genetic analysis described here indicates that sel-12 facilitates lin-12-mediated reception of intercellular signals. sel-12 might be directly involved in lin-12-mediated reception, functioning for example as a co-receptor or as a downstream effector that is activated upon LIN-12 activation.

Alternatively, sel-12 may be involved in a more general cellular process such as receptor localization or recycling and hence influence lin-12 activity indirectly. Although the remarkable conservation of sel-12 and S182 does not provide any immediate indication of the function of S182 in the Alzheimer's disease process, it is striking that 4 of the 5 mutations found in affected individuals alter amino acids that are identical in SEL-12 and S182 (see FIG. 2). The powerful tools of classical and molecular genetic studies in *C. elegans*, including the ability to identify extragenic suppressor and to generate transgenic lines containing engineered genes, can now be brought to bear on fundamental issues of SEL-12/S182 structure and function.

References of the First Series of Experiments

1. Greenwald, I. *Current Opinion in Genetics and Development* 4, 556–562 (1994).
2. Artavanis-Tsakonas, S., Matsuno, K. & Fortini, M. *Science* 268, 225–268 (1995).
3. Greenwald, I., Sternberg, P. & Horvitz, H. R. *Cell* 34, 435–444 (1983).
4. Ferguson, E. L. & Horvitz, H. R. *Nature* 110, 259–267 (1985).
5. Brenner, S. *Genetics* 77, 71–94 (1974).
6. Kimble, J. & Hirsh, D. *Developmental Biology* 81, 208–221 (1979).
7. Kimble, J. *Developmental Biology* 87, 286–300 (1981).
8. Seydoux, G. & Greenwald, I. *Cell* 57, 1237–1245 (1989).
9. Greenwald, I. & Seydoux, G. *Nature* 346, 197–199 (1990).
10. Sundaram, M. & Greenwald, I. *Genetics* 135, 755–763 (1993).
11. Sulston, J. & White, J. *Developmental Biology* 78, 577–597 (1980).
12. Sternberg, P. & Horvitz, H. R. *Cell* 44, 761–772 (1986).
13. Sulston, J. & Horvitz, H. R. *Developmental Biology* 56, 110–156 (1977).
14. Horvitz, H. R. & Sternberg, P. W. *Nature* 351, 535–541 (1991).
15. Simske, J. S. & Kim, S. K. *Nature* 375, 142–146 (1995).
16. Tuck, S. & Greenwald, I. *Genes and Development* 9, 341–357 (1995)
17. Sternberg, P. W. *Nature* 335, 551–554 (1988).
18. Sternberg, P. W. & Horvitz, H. R. *Cell* 58, 679–693 (1989).
19. Beitel, G. J., Clark, S. G. & Horvitz, H. R. *Nature* 348, 503–509 (1990).
20. Han, M. & Sternberg, P. W. *Cell* 63, 921–931 (1990).
21. L'Hernault, S. W. & Arduengo, P. M. *The Journal of Cell Biology* 119, 55–68 (1992).
22. Sherrington, R., et al. *Nature* 375, 754–760 (1995).
23. Lambie, E. & Kimble, J. *Development* 112, 231–240 (1991).
24. Priess, J. R., Schnabel, H. & Schnabel, R. *Cell* 51, 601–611 (1987).
25. Austin, J. & Kimble, J. *Cell* 51, 589–599 (1987).
26. Khan, A. S., et al. *Nature genetics* 2, 180–185 (1992).
27. Coulson, A., Waterston, J., Kiff, J., Sulston, J. & Kohara, Y. *Nature* 235, 184–186 (1988).
28. Mello, C. C., Kramer, J. M., Stinchcomb, D. T. & Ambros, V. A. *EMBO Journal* 10, 3959–3970 (1991).
29. Maniatis, T., Fritsch, E. F. & Sambrook, J. *Molecular cloning: A laboratory manual* (Cold Spring Harbor Laboratory, Cold Spring Harbor, 1982).
30. Krause, M. & Hirsh, D. *Cell* 49, 753–761 (1987).
31. Ohara, O., Dorit, R. & Gilbert, W. *Proceedings of the National Academy of Sciences* 86, 5673–5677 (1989).

Second Series of Experiments

Background and Significance

Alzheimer's disease is a devastating and common disease of the central nervous system, and studies of familial forms have identified a number of loci that are implicated in the development of the disease. Two loci, S182 (AD3) (Sherrington et al., 1995) and STM2 (Levy-Lahad et al., 1995a,b), which is also known as E5-1 (Rogaev et al., 1995), have recently been found to be associated with the development of early onset familial Alzheimer's disease. These loci encode related proteins with multiple transmembrane domains.

The *C. elegans* model described here is based on the finding that the sel-12 gene encodes a protein that is highly similar to S182 and STM2 (Levitan and Greenwald, 1995; see FIG. 1). For example, SEL-12 and S182 are 48% identical over 460 amino acids. The remarkable conservation of the SEL-12 and S182 predicted protein structure suggests that their functions are likely to be conserved as well. Furthermore, it is striking that seven of the eight changes in S182 that are associated with early-onset familial Alzheimer's disease (Rogaev et al., 1995; Sherrington et al., 1995; see FIG. 1) alter amino acids that are identical in SEL-12, and that the eighth alters an amino acid that has been changed very conservatively during evolution, and two out of two changes in STM2/E5-1 that are associated with Alzheimer's disease (Levy-Lahad et al., 1995b; Rogaev et al., 1995) affect amino acids that are identical in SEL-12.

Applicants hope to bring the powerful tools of classical and molecular genetic studies in *C. elegans* to bear on fundamental issues of SEL-12/S182/STM2 structure and function. Thus far, proteins similar to LIN-12/Notch and SEL-12/S182/STM2 have not been described in single-celled organisms (for example, >95% of the yeast genome has been sequenced and has not yielded any similar proteins), so *C. elegans* may be the simplest practical system for studying these issues in vivo.

Preliminary Studies sel-12. Applicants identified sel-12 [sel=suppressor/enhancer of lin-12] by screening for suppressors of the "Multivulva" phenotype caused by an allele of lin-12 that causes constitutive LIN-12 activation. Applicants performed a genetic and molecular characterization of sel-12 (Levitan and Greenwald, 1995), which established: (1) Reducing or eliminating sel-12 activity reduces the activity of lin-12 and of glp-1, another member of the lin-12/Notch family. In addition, reducing or eliminating sel-12 activity causes an egg-laying defective (Egl) phenotype. Applicants do not know if the Egl phenotype is a direct consequence of reducing lin-12 activity (Sundaram and Greenwald, 1993a) or an independent effect of reducing sel-12 activity. (2) sel-12 and lin-12 can functionally interact within the same cell. (3) sel-12 is predicted to encode a protein with multiple transmembrane domains that is highly similar to S182 and STM2, which have been implicated in early-onset familial Alzheimer's disease (Levy-Lahad et al., 1995a, b; Rogaev et al., 1995; Sherrington et al., 1995). The presence of multiple transmembrane domains is consistent with SEL-12 function as a receptor, ligand, channel or membrane structural protein.

The fact that the only striking phenotype caused by sel-12(ar171) is a defect in egg-laying may reflect the fact that egg-laying is particularly sensitive to reduction in lin-12 activity (Sundaram and Greenwald, 1993a; H. Wilkinson and I. G., unpublished observations). The egg-laying defect may reflect an as yet unidentified cell fate decision(s), or alternatively may also be viewed as a late-onset behavioral phenotype. However, the fact that sel-12(ar171) mutants do not display all of the defects associated with loss of lin-12 function may indicate that sel-12(ar171) is not a null allele, despite the severe truncation in protein product it is expected to cause; alternatively, sel-12 function may be partially redundant with the function of another gene.

Applicants identified a genomic fragment capable of complementing sel-12 alleles (Levitan and Greenwald, 1995).

Some of the experiments described in this invention require the ability to express reporter genes or altered sel-12 genes appropriately. An expression method developed in applicants, laboratory will enable these experiments to be performed. (1) Applicants have developed a vector that expresses inserted cDNAs under the control of lin-12 regulatory sequences (pLEX; Struhl et al., 1993). The applicants have found that construct containing a sel-12 cDNA in the pLEX vector is capable of rescuing sel-12 mutants. (2) Applicants have developed an analogous vector, p1B7, that should express inserted cDNAs under the control of sel-12 regulatory sequences. p1B7 is based on a genomic fragment that is capable of rescuing sel-12 mutants (Levitan and Greenwald, 1995): a unique BamHI site was inserted at +1 into a genomic fragment capable of complementing a mutant allele, thereby destroying the first codon of the gene. The expression vector contains 3.5 kb of 5' flanking region (2.5 kb more than the original rescuing fragment of Levitan and Greenwald, 1995) and 0.5 kb of 3' flanking region.

These vectors are used as follows (Wilkinson et al., 1994; Fitzgerald and Greenwald, 1995; Wilkinson and Greenwald, 1995). A cDNA containing its own start and stop codons, but lacking a polyadenylation signal, is inserted into the vector. The resulting transcript is predicted to contain an unusually long 3' untranslated region (UTR). These aberrant 3' UTRs are generally destabilizing, leading to very low levels of detectable expression. However, this problem can be overcome by placing the transgenes in a smg mutant background, which stablizes mRNAs with long 3' untranslated regions (Pulak and Anderson, 1993). The recent identification of a temperature-sensitive smg-7 mutation (B. Cali and P. Anderson, personal communication) enables transgenic lines to be generated at the permissive temperature (15°), where smg-7(ts) has nearly wild-type activity, and shifted to the restrictive temperature (25°) for the analysis of mutant phenotypes (K. Fitzgerald, personal communication).

lin-12. lin-12 is the archetype of the "lin-12/Notch gene family" of putative transmembrane receptor proteins that is found throughout the animal kingdom (reviewed in Greenwald and Rubin, 1992; Artavanis-Tsakonas et al., 1995). Members of this family are transmembrane proteins with repeated epidermal growth factor (EGF)-like motifs and LIN-12/Notch repeat motifs in their extracellular domains, and "cdc10/SWI6" motifs (also termed "ankyrin repeats") in the intracellular domains. In C. elegans and Drosophila, lin-12/Notch family members were first defined genetically, by mutations that alter cell fate decisions that involve cell-cell interactions during development (reviewed in Greenwald and Rubin, 1992). In vertebrates, lin-12/Notch genes were identified either by cross-hybridization with Notch probes, or, more revealingly, by oncogenic mutations: mutation of int-3 by mouse mammary tumor virus is associated with the development of breast cancer in mice (Gallahan and Callahan, 1987; Robbins et al., 1992) and mutation of TAN-1 is associated with T cell leukemias in people (Ellisen et al., 1991; Robbins et al., 1992).

The nature of the relationship between lin-12 and sel-12 is uncertain. lin-12/Notch genes specify many different cell fate decisions in C. elegans and Drosophila, and in both organisms some of these decisions are critical for neurogenesis. As described above, the initial genetic analysis indicated that sel-12 facilitates lin-12-mediated reception of intercellular signals (Levitan and Greenwald, 1995). sel-12 might be directly involved in lin-12-mediated reception, functioning for example as a co-receptor or as a downstream effector that is activated upon LIN-12 activation. Alternatively, sel-12 may be involved in a more general cellular process such as receptor localization or recycling and hence influence lin-12 activity indirectly. The powerful tools of classical and molecular genetic studies in C. elegans, including the ability to identify extragenic suppressors and to generate transgenic lines containing engineered genes, can now be brought to bear on fundamental issues of SEL-12/S182/STM2 structure and function.

Research Design and Methods

I. Basic Characterization of sel-12.

A. Additional basic characterization of sel-12. There are several lines of experimentation that, along with previous work (Levitan and Greenwald, 1995), will constitute the basic characterization of sel-12.

(1) Null phenotype. Although sel-12(ar171) is predicted to encode a protein that is truncated by half, it is conceivable that this portion of the protein retains some activity and that sel-12(ar171) is not a true null allele [sel-12(ar171) mutants have normal mRNA levels]. Null alleles will be used to reveal the requirement for gene activity, for gene dosage studies, and as a background into which engineered sel-12 mutations can be introduced. Applicants will therefore isolate additional sel-12 alleles by complementation screening as described in Levitan and Greenwald (1995), with the goal of identifying an internal deletion of sel-12 or an allele associated with a stop codon early in the gene. If alleles with early stops or internal deletions cause a more severe phenotype than sel-12(ar171), applicants will analyze the phenotype in detail. Alleles with other properties may also be obtained from the screen+may be useful for other experiments, such as drug testing.

(2) Expression pattern. Using the expression vector p1B7 applicants have engineered a sel-12::lacZ reporter gene. The lacZ gene used contains a nuclear localization signal (Fire et al., 1990), which facilitates the identification of individual cells. A developmental profile of expression will be determined. Preliminary results indicate that sel-12::lacZ is more broadly expressed than lin-12::lacZ (Wilkinson and Greenwald, 1995), including much expression in the nervous system.

(3) Behavioral defects. Besides the Egl defect of hermaphrodites, there may be other behavioral defects. For example, preliminary results suggest that sel-12(ar171) males display behavioral abnormalities that affect mating efficiency. Applicants will examine this potential defect further using mating assays (Hodgkin, 1983; Liu and Sternberg, 1994). The sel-12::lacZ expression pattern may provide clues for behaviors that may be affected in sel-12 mutants.

(4) SEL-12 antibodies. Applicants will use standard methods (Harlow and Lane, 1988) to generate antibodies to SEL-12. The antibodies will be useful for examining protein localization: the localization of wild-type and mutant SEL-12 proteins in otherwise wild-type backgrounds and in suppressor mutant backgrounds.

(5) Identification of C. elegans genes that are highly related to SEL-12. One possible reason that the phenotype of sel-12(ar171) is of relatively limited severity is that sel-12 is partially functionally redundant with another gene or genes.

Functional redundancy might be reflected in sequence similarity. The *C. elegans* spe-4 gene (L'Hernault and Arduengo, 1992) is weakly related to sel-12 (see FIG. 1) and in collaboration with Steve L'Hernault (Emory University), applicants will express a spe-4 cDNA under the control of sel-12 or lin-12 regulatory sequences, to see if SPE-4 can replace SEL-12. Applicants will also examine the phenotype of spe-4; sel-12 double mutants to see if the double mutant has a more sever phenotype than either single mutant.

If more closely related genes exist, applicants can easily identify them by periodically searching the database of the *C. elegans* sequencing project, which is currently 25% complete; and is expected to be fully completed by 1998 (R. Waterston et al., personal communication). It may also be possible to identify sel-12 related genes by low-stringency hybridization (Sambrook et al., 1989) and/or screening an expression library with SEL-12 antibodies (Harlow and Lane, 1988). If any method identifies genes that are related to sel-12, applicants will express them under the control of sel-12 or lin-12 regulatory sequences to see if they can functionally replace sel-12. If so, then applicant will attempt to generate null alleles of the sel-12-related gene, using a Tc1 transposon-based excision method (Rushforth et al., 1993; Zwaal et al., 1993; Greenwald et al., 1994), unless better gene "knock-out" technology becomes available. The phenotype of null mutants will be examined alone, and in combination with sel-12(null).

It is also possible that genes similar to sel-12 will be revealed by the analysis of other genes identified by reverting alleles of lin-12 (Sundaram and Greenwald, 1993b; J. Thomas, F. Tax, E. Ferguson and H. R. Horvitz, personal communication; D. Levitan and I. Greenwald., unpublished observations).

B. Functional equivalence of S182, STM2 and SEL-12. There is high degree of similarity between SEL-12, S182, and STM2, which suggests they have similar biochemical functions and properties. The best test of this hypothesis would be to demonstrate that S182 and STM2 can substitute for SEL-12. Applicants will place the human cDNAs under the control of sel-12 regulatory sequences, using the p1B7 expression vector and will assess the ability of S182 or STM2 to replace SEL-12 in *C. elegans*.

II. Engineered sel-12 Transgenes ["sel-22(Alz)"] containing Alterations Associated With Early-onset Familial Alzheimer's Disease The experiments in this section of the proposal are designed to help understand the consequences of mutation of S182 and STM2 for protein function. Mutations that alter the SEL-12 protein so that they resemble mutant proteins associated with familial early-onset Alzheimer's disease will be created. Because genetic analysis in *C. elegans* has revealed the phenotypic consequences of reducing sel-12 activity as well as the phenotypic consequences of both reduced and elevated lin-12 activity, genetic analysis of phenotypes associated with sel-12(Alz) mutations will reveal the effect of S182 and STM2 mutations on S182 and STM2 function.

A. Generation of transgenic *C. elegans* lines. Applicants will create engineered sel-12 transgenes containing alterations associated with early-onset familial Alzheimer's disease in people. Applicants will engineer the changes using standard PCR-based strategies in a clone of sel-12 genomic DNA. These clones will be microinjected into lin-12(+); sel-12(+) *C. elegans* (either the wild-type strain N2 or usefully marked derivatives) to establish transgenic lines (Fire, 1986; Mello et al., 1991), which will be analyzed for mutant phenotypes and for interactions with lin-12. The rol-6(su1004) gene (Mello et al., 1991) will be used as a cotransformation marker; other cloned genes may be used as cotransformation markers to facilitate phenotypic analysis, which can be difficult in Roller mutants, if necessary. Several different concentrations of injected DNA will be tried.

TABLE 3

| Human gene | Mutation | SEL-12 residue |
|---|---|---|
| S182 | M146L | M115 |
|  | H163R | H132 |
|  | A246E | V215 |
|  | A260V | A229 |
|  | A285V | A254 |
|  | L286V | L255 |
|  | L382V | L371 |
|  | C410Y | C387 |
| STM2 | N141I | N104 |
|  | M239V | M202 |

Table 3. Mutations associated with the development of Alzheimer's disease (Levy-Lahad et al., 1995; Rogaev et al., 1995; Sherrington et al., 1995), and the corresponding amino acid in SEL-12 (see also FIG. 1). Note that nine of ten mutations in S182 or STM2 affect amino acids that are identical in SEL-12. The tenth, S182 A246E, causes a dramatic change in a residue that is conservatively different between S182 and SEL-12.

If the sel-12(Alz) mutations cause dominant lethal or sterile phenotypes that prevent the establishment of transgenic lines, applicants will use an alternative strategy to achieve conditional or more limited expression. The engineered mutations will be incorporated into a sel-12 cDNA, which can be cloned into a sel-12 expression vector applicants have made (see "Background and Preliminary Studies"): in this vector, the ATG of the cloned sel-12(+) gene has been replaced by a BamHI linker, so that cDNAs can be cloned into the unique BamHI site and expressed under the control of sel-12 regulatory sequences. Efficient expression should be obtained in a smg mutant background, so that transgenic arrays may be generated in a smg(+) background and crossed into a smg background,for analysis, or generated in a smg-7(ts) background at the permissive temperature (15°) and analyzed at the restrictive temperature (25°). The temperature-sensitive smg-7 mutant will be particularly useful, since transgenic worms may be shifted at different times during development, and the effects on different cell fate decisions examined.

Applicants can also clone the mutant sel-12 cDNAs into a lin-12 expression vector (Struhl et al., 1993), which has a more restricted pattern of expression (defined by Wilkinson et al., 1994; Wilkinson and Greenwald, 1995) and hence may be less deleterious. Although heat shock promoter-based vectors are available, in applicants' experience they have not been reliably effective for studies of lin-12-mediated cell fate decisions, probably because of tissue-specificity of the heat shock promoters (see Stringham, Fire). However, they may be useful for examining the consequences of altered sel-12 coding regions in other tissues, or for ectopic expression experiments.

Applicants can also perform analogous experiments using mutated human S182 or E5-1/STM2 cDNAs cloned into p1B7 or pLEX.

Applicants will create integrated lines for phenotypic analysis. In *C. elegans*, the microinjection technique used to establish transgenic lines generally results in lines containing extrachromosomal arrays of injected DNAs. Such extrachromosomal arrays may be integrated by irradiation (Hedgecock and Herman, 1995), so that arrays become inserted randomly into the genome. Such lines generally have more reproducible expression from the transgenes, and avoid complications for phenotypic analysis introduced by the potential for somatic mosaicism of extrachromosomal arrays.

B. Phenotypic analysis of transgenic lines containing sel-12(Alz) genes. Integrated lines carrying sel-12(Alz) genes will be analyzed for viability and fertility. They will also be examined for the Egl phenotype associated with reduced sel-12 activity (Levitan and Greenwald, 1995), and other phenotypes that may be revealed by the analysis described in section I of this proposal. They will also be analyzed for phenotypes associated with reduced lin-12 activity (such as 2 anchor cells, no 2° vulval precursor cell lineages, ventral coelomocytes/missing sex muscles; Greenwald et al., 1983; Sundaram and Greenwald, 1993a) or elevated lin-12 activity (such as no anchor cell, ectopic 2° vulval precursor cell lineages, extra sex muscles/no dorsal coelomocytes; Greenwald et al., 1983), and reduced glp-1 activity (such as germline proliferation defect, missing anterior pharynx or extra pharyngeal cells; Austin and Kimble, 1987; Priess et al., 1987; Bowerman et al., 1994; Mello et al., 1994) or elevated glp-1 activity (Fitzgerald and Greenwald, 1995; tumorous germ line; L. W. Berry and T. Schedl, personal communication).

If it is necessary to use a conditional expression system to generate the lines, transgenic animals will be examined after a shift from the permissive to the restrictive temperature at different times during development.

If antibodies to SEL-12 are available, the localization of wild-type and mutant SEL-12 proteins will be examined by examining stained whole-mounts by confocal microscopy and possibly by immunoelectron microscopy.

C. Genetic analysis of sel-12(Alz) genes. The S182 and STM2 mutations associated with early onset Alzheimer's disease in people are dominant. The most likely possibility is that altered gene activity underlies this dominance, since ten different mutations in S182 and STM2 are missense mutations in conserved amino acids. Dominant mutations may cause a mutant protein to have elevated activity, decreased activity, or aberrant activity. Genetic tests can be used to distinguish these possibilities, and are particularly valuable when biochemical function is not known or when biochemical assays are difficult to execute on mutant proteins. Thus, the ability to assess the genetic properties of the sel-12(Alz) transgenes in *C. elegans*, where rigorous genetic tests to determine the consequences of mutation on gene activity are possible, may be very valuable for understanding the effect of the mutations on Alzheimer's disease loci in people.

If sel-12(Alz) mutations cause dominant phenotypes in *C. elegans* (i.e., phenotypes in a sel-12(+) background), applicants will examine them by adapting classical gene-dosage tests (Muller, 1932) for hypermorphic (elevated), neomorphic (novel) or antimorphic (dominant-negative) activity. Two approaches will be used. First, established arrays carrying sel-12(Alz) genes will be crossed into sel-12(ar171) mutants, and into sel-12(+) hermaphrodites carrying a duplication of sel-12(+). Second, additional arrays will be established by coinjection of sel-12(Alz) with sel-12(+) genes. If a sel-12(Alz) mutation is a hypermorph, then the severity of the mutant phenotype should increase as additional doses of sel-12(+) are added. If a sel-12(Alz) mutation is a neomorph, then the severity of the mutant phenotype should be essentially unchanged as additional doses of sel-12(+) are added. If a sel-12(Alz) mutation is an antimorph, then the severity of the mutant phenotype should decrease as additional doses of sel-12(+) are added.

If sel-12(Alz) does not cause a phenotype in a sel-12(+) background, the sel-12 activity of the transgenes will be assessed by placing the transgenes into a sel-12(ar171) or sel-12(null) background. If the sel-12(Alz) transgenes do not have rescuing activity, then applicants will not be able to draw any rigorous conclusions.

III. Identification and Characterization of Extragenic Suppressors of sel-12(ar171) and sel-12(Alz)

Extragenic suppressor mutations may identify new genes that are involved in SEL-12/S182/STM2-mediated processes. Even if suppressor mutations identify genes that were defined previously, they will reveal a functional connection with sel-12/S182/STM2. Genetic and molecular characterization of these "suppressor genes" in *C. elegans* will reveal the nature of their interactions with sel-12 and lin-12. Furthermore, if suppressor mutations, or other alleles of suppressor genes that can be subsequently generated (such as null alleles), have highly-penetrant, easily scored phenotypes, they too can be reverted to identify additional genes that may be involved in sel-12 function. In this way, a network of interacting genes can be identified, and the normal function, as well as the aberrant function in mutants, can be elucidated.

A potential outcome of the suppressor analysis is an insight into the biochemistry of SEL-12/S182/STM2-mediated processes. The best outcome will be if one of the suppressor genes has a known biochemical activity (based on sequence analysis). This information will be combined with the results of genetic analysis suggesting the nature of the interaction of the suppressor mutations with sel-12, and will potentially be useful for the design and testing of therapeutic agents in both *C. elegans* and mammalian models, and ultimately for people. A second important reason is that human homologs of the suppressor genes themselves may be useful diagnostic reagents. For example, such cloned genes might be used to analyze human pedigrees to reveal the underlying defects in other inherited forms of Alzheimer's disease (and will possibly have some use for sporadic forms as well).

A. Reversion of sel-12(ar171). sel-12(ar171) causes a highly penetrant Egl phenotype. Applicants will generate Egl$^+$ revertants by mutagenizing sel-12(ar171) hermaphrodites with ethyl methanesulfonate (EMS) (Brenner, 1974) and screening for Egl$^+$(normal egg-laying) revertants in the $F_1$, $F_2$ and $F_3$ generations. This procedure will enable the identification of dominant, recessive and maternal effect suppressor mutations.

Applicants performed a pilot mutagenesis, which indicated that this procedure will yield suppressor mutations: applicants identified two suppressor mutations, including a dominant suppressor that maps near dpy-10 II (D. Brousseau, personal communication), in a region of the genome that has been well characterized genetically (e.g., Sigurdson et al., 1984) and sequenced (R. Waterston et al., personal communication). The suppressor mutations appeared to arise at low frequency, suggesting that they may be specific alterations and not null alleles, but applicants did not perform careful quantitation in their pilot experiment. Future mutageneses for suppressor mutations will be performed quantitatively (see e.g., Greenwald and Horvitz, 1980).

B. Reversion of sel-12(Alz) mutants. If sel-12(Alz) mutations cause a highly penetrant phenotype (such as lethality, sterility, or egg-laying defect), applicants will mutagenize integrated lines and look for revertants.

C. Analysis of suppressor ("sup") mutations.

(1) Basic genetic analysis. This analysis will include:

(a) Mapping and complementation tests. Applicants will determine if the sup mutation is recessive or dominant, precisely map the suppressor mutations and perform complementation testing with candidate genes in the region, and perform inter se complementation testing among recessive sup mutations mapping in the same region.

(b) Phenotypic analysis. The phenotype of sup mutations in a sel-12(+) background, and in combination with lin-12 activated (Greenwald et al., 1983; Greenwald and Seydoux, 1990; Struhl et al., 1993), lin-12 hypomorphic (Sundaram and Greenwald, 1993a), and lin-12(null) (Greenwald et al., 1983) alleles will be examined. The localization of wild-type and mutant SEL-12 proteins will be examined by examining stained whole-mounts by confocal microscopy and possibly by immunoelectron microscopy.

(c) Gene dosage studies. Genetic studies will be used to illuminate the effect of the sup mutation on sup gene activity. For a recessive suppressor, the relative suppression of sup/Df and sup/sup will be compared; these genotypes will also; be examined for additional phenotypes. The genotype sup/sup/+ will also be examined if an appropriate duplication is available, since it is possible that the sup mutations are recessive gain-of-function and require two copies to suppress sel-12 mutations.

For a dominant suppressor, the relative suppression of sup/Df, sup/+ and sup/+/+ will be compared, by examining the ability to suppress sel-12 mutations and by analyzing any associated mutant phenotypes. The rationale is the same as described above: if a sup mutation is a hypermorph, then the suppression ability (and/or an associated phenotype) should increase as additional doses of sup-?(+) are added; if sup is a neomorph, then the suppression ability (and/or phenotype) should be essentially unchanged as additional doses of sup-?(+) are added; and if a sup mutation is an antimorph, then the suppression ability (and/or mutant phenotype) should decrease as additional doses of sel-12(+) are added.

(d) Null phenotype of sup genes. If sup mutations are not null alleles, then applicants will perform screens for null mutations. For example, if the sup mutations are recessive partial loss-of-function mutations and are viable and fertile in trans to a deficiency, then applicants can screen for sup/*; sel-12 hermaphrodites that are suppressed (where *=mutagenized chromosome) (see e.g. Greenwald and Horvitz, 1980). If the sup mutations are dominant, then applicants can screen for loss of dominant suppressor activity in sup */+; sel-12 hermaphrodites (see e.g. Greenwald and Horvitz, 1982). The null phenotype of sup loci may reveal the normal role of sup genes.

(2) Molecular analysis. The first phase of molecular analysis involves the molecular cloning and DNA sequence analysis of suppressor genes. Transposon tagging (Greenwald, 1985; Moerman et al., 1986), or transformation screening of clones from the well-correlated genetic and physical maps (Coulson et al., 1988 and personal communication) can be used to clone genes in C. elegans. The details of such strategies require the completion of the genetic analysis of the suppressor mutations. A general overview of such strategies is given below.

Transposon-tagging: Suppressor genes may be cloned by screening for transposon-associated alleles, using the same strategies as can be used for identifying null alleles described above. Potential transposon-associated alleles can be screened by Southern blotting, using transposon probes (e.g., Greenwald, 1985; Moerman et al., 1986), or cosmids in the region provided by the genome project.

Transformation screening: Suppressor genes defined by loss-of-function or antimorphic (dominant-negative) mutations may be cloned by transformation "antisuppression": cloned cosmids provided by the genome project may be used to establish transgenic arrays that complement sup mutations, thereby reversing their ability to suppress mutations in sel-12. This strategy may also be adapted to clone suppressor genes defined by gain-of-function hypermorphic or neomorphic mutations. After a sup mutation has been mapped to a small region of;the physical map, cosmids from the region can be used to probe a Southern blot of DNA made from the sup mutant, in the hopes of identifying an altered restriction fragment associated with the sup mutation. If an alteration is not detected, then a modified transformation screening approach may be used. A library can be made from a sup mutant, and DNA from the region can be identified by probing with mapped cDNAs from the region provided by the genome project. The potential sup containing cosmids can be verified by restriction mapping or DNA fingerprinting (Coulson et al., 1986), and used for transformation experiments based on their dominant suppressor activity.

Identification of other genes whose activities are influenced by sel-12. Applicants are testing the genetic interaction of sel-12 alleles with mutations in other secreted or transmembrane proteins by constructing and analyzing double mutants. This information may reveal other pathways that involve sel-12 activity, and may suggest other human diseases for which sel-12 is relevant.

Identification of other genes involved in sel-12-mediated proc sees by the yeast two-hybrid system. Applicants will apply the yeast two-hybrid system to screen a cDNA library for potential interacting proteins and to screen directly for interaction with LIN-12 and GLP-1. The two-hybrid screen, originally developed by Fields and Song (1989), is a powerful strategy for identifying potential interacting proteins. The screen relies on the ability of GAL4 to activate transcription of a reporter gene containing GAL4 upstream activation sequences. GAL4 has a DNA binding domain (GBD) and an activation domain (GAD). Normally, the two domains are present in the same polypeptide; if they are separated, GAL4 activity is abolished. However, if the separated domains are joined to protein sequences that interact with each other, the two domains are brought together, and GAL4 activity is restored. Thus, a yeast strain containing a "bait" fused to the GBD is transformed with a library containing potential GAD fusions, and a selection or screen for reconstituted GAL-4 activity is used to identify candidates.

The virtue of conducting such a screen in C. elegans is the potential for genetic analysis of candidate genes, since in the absence of a functional analysis it is possible that physical interactions revealed by the two-hybrid method are not meaningful in vivo. Mutations that reduce or eliminate the activity of the candidate gene will be analyzed in C. elegans. If the candidate clone maps to a genetically well-characterized region, applicants will try transformation rescue of the extant mutations. Alternatively, null alleles will be identified using PCR-based screens (Rushforth et al., 1993; Zwaal et al., 1993; Greenstein et al., 1994). The consequences of elevating candidate gene activity will be examined by creating high copy number transgenic lines or by overexpressing the candidate gene in wild-type and mutant backgrounds. Any candidate genes that appear to be involved in SEL-12-mediated processes by genetic analysis can be used in the same way the suppressor "sup" genes described above could be used.

The use of sel-12 mutants for screening for compounds that may ameliorate Alzheimer's disease, and possibly other diseases caused by affecting the activity of members of the SEL-12/S182/STM2 family. sel-12 mutants generated by standard genetic and transgenic methods may be use for drug testing. This approach is potentially beneficial for two reasons. First using C. elegans, the applicants can analyze the effect of drugs on sel-12 activity even though the biochemical function of sel-12 is not known, based on the suppression or enhancement of sel-12 mutant phenotypes (i.e, egg-laying defect and other phenotypes that will be identified, or the effects of altering sel-12 activity on lin-12 activity). For example, the proportion of egg-laying competent sel-12(ar131) or sel-12(ar171) mutant hermaphrodites may be compared when the mutant worms are cultured in the presence of candidate compounds; an increase in the proportion of egg-laying competent worms in the presence of compound would indicate that sel-12 activity is increased or bypassed. sel-12 mutants may also be transiently treated with candidate compounds. If the sel-12(Alz) mutations have additional or different phenotypic consequences, transgenic lines containing sel-12(Alz) transgenes may also be used to screen for the effect of compound on sel-12(Alz) activity. Second, C. elegans is easy and inexpensive to cultivate. Thus, a preliminary screening of the effect of compounds on sel-12 mutants may help to set priorities for drug testing in mammalian system, thereby reducing the expense and shortening the amount of time it takes to identify potential therapeutic agents.

Since sel-12 mutations affect lin-12 activity, and mammalian homologues of lin-12 have been implicated in oncogenesis, it is possible that the identification of compounds that influence sel-12 activity will have implications for cancer, and possibly other human diseases.

Implications of suppressor genes for drug testing. Suppressor genes defined genetically, and candidates defined using the yeast two-hybrid system, encoding proteins of known biochemical function will be useful for targeted drug design or the development of diagnostic tests for Alzheimer's disease or other diseases associated with alteration of members of the SEL-12/S182/STM2 family. For example, if a suppressor gene encodes a protein with an enzymatic activity, competitive or noncompetitive inhibitors of the enzyme might be effective drugs.

Suppressor genes encoding proteins of unknown biochemical function will also be useful for drug development. For example, the use of ribozymes based on suppressor genes, or the delivery via liposomes of vectors expressing suppressor genes, are potential therapeutic applications. The genetic analysis in C. elegans will provide a guide as to the nature of suppressor mutations. For example, a mutation that suppresses a sel-12(Alz) mutation that increases the activity of the suppressor gene would suggest the second strategy.

Implications of suppressor genes for diagnostic tests. The genetically-defined suppressor genes or candidate genes obtained using the yeast-two hybrid system will be used, to identify human homologues. The cloned human homologues will be used to analyze pedigrees to see if mutations of the suppressor loci are associated with the development of Alzheimer's disease or other diseases. For example, the E5-1 gene was identified by using a cloned gene for pedigree analysis (Rogaev et al., 1995).

Suppressor genes may also be used as the basis for diagnostic tests. For example, mutations in suppressor genes implicated in Alzheimer's disease will be detected at the DNA level by Southern blotting or PCR/sequencing analysis, or at protein level, by Western blotting, immunoprecipitation or staining of cells or tissues.

Antibodies for diagnosis. Antisera to SEL-12 may cross-react with S182 and/or E5-1/STM2. Furthermore, peptides designed on the recognition of highly conserved regions, revealed by alignment of the predicted protein sequences of SEL-12, S182, and E5-1/STM2, or of SEL-12, S182, E5-1/STM2, and SPE-4(see FIG. 2), may be useful as diagnostic reagents. The conserved regions may reveal salient characteristics of a family of proteins, two of which have already been implicated in early-onset Alzheimer's disease. Such antisera could also be used to identify other members of the family, by screening expression libraries (Harlow and Lane, 1988).

References of the Second Series of Experiments

Artavanis-Tsakonas, S., Matsuno, K. and Fortini, M. E. (1995) Science 268: 225–232.

Austin, J. and Kimble, J. (1987). glp-1 is required in the germline for regulation of the decision between mitosis and meiosis in C.elegans. Cell 51,589–599.

Brenner, S. Genetics 77, 71–94 (1974).

Coulson, A. Sulston, J., Brenner, S., and Karn, J. (1986) Proc. Natl. Acad. Sci. (USA) 83,7821–7825.

Coulson, A., Waterston, J., Kiff, J., Sulston, J. and Kohara, Y. Nature 235, 184–186 (1988).

Ellisen, L. W., Bird, J., West, D. C., Soreng A. L., Reynolds, T. C. Smith, S. D., Sklar, J. (1991) Tan-1, the Human homologue of the Drosophila Notch gene is Broken by chromosomal translocations in T lymphoblastic neoplasms. Cell 66,649–661.

Fields, S. and Song, O. K. (1989) A novel genetic system to detect protein-protein interactions. Nature 340, 245–246.

Fire, A. (1986) Integrative transformation of Caenorhabditis elegans. EMBO J. 5,2673–2680.

Fire, A. Harrison. S. W. and Dixon, D. (1990) A modular set of lacZ fusion vectors for studying gene expression in Caenorhabditis elegans. Gene 93, 189–198.

Fitzgerald, K. and Greenwald, I. (1995) Interchangeability of C. elegans DSL proteins and intrinsic signalling activity of their extracellular domains in vivo. Development, in press.

Gallahan, D. and Callahan, R. (1987) Mannary tumorigenesis is feral mice: identification of a new int locus in mouse mammary tumor virus (CzechII)-idenced mammary tumors. J. Virol. 61, 66–74.

Greenwald, I. and Rubin, G. M. (1992) Making a difference: the role of cell-cell interactions in establishing separate identities for equivalent cells. Cell 68, 271–281.

Greenwald, I. Cell 43, 583–590 (1985).

Greenwald, I. S. and Horvitz, H. R. Genetics 96, 147–164 (1980).

Greenwald, I. S. and Horvitz, H. R. Genetics 101, 211–225 (1982).

Greenwald, I. S., Sternberg, P. W. and Horvitz, H. R. Cell 34, 435–444 (1983).

Greenwald, I. and Horvitz, H. R. Genetics 113, 63–72 (1986).

Greenwald, I. S., Sternberg, P. W. and Horvitz, H. R. Cell 34, 435–444 (1983).

Hedgecock, E. M., Culotti, J. G. Hall, D. H. and stern, B. D. (1987) Genetics of cell and axon migrations in Caenorhabditis elegans. development 100:365–387.

Hodgkin, J. (1983) Genetics 103: 43–64.

Hodgkin, J., Papp, A., Pulak, R., Ambros, V. and Anderson, P. (1989) A new kind of informational suppression in the nematode Caenorhabditis elegans. Genetics 123, 301–313.

Levitan, D. and Greenwald, I. Nature, accepted for publication (1995).

Levy-Lahad, E. et al. (1995a) A familial Alzheimer's disease locus on chromosome 1. Science 269: 970–973.

Levy-Lahad, E. et al. (1995b) Candidate gene for the chromosome 1 familial Alzheimer's disease locus. science 269: 973–977.

Mello, C. C., Kramer, J. M., Stinchcomb, D. and Ambros, V. (1991) Efficient gene transfer in *C. elegans*: extrachromosomal maintenance and integration of transforming sequences. EMBO J. 10, 3959–3970.

Moerman, D. G., Benian, G. M. and Waterston, R. H. *Proceedings of the National Academy of Sciences* 83, 2579–2583 (1986).

Muller, H. J. (1932) Further studies on the nature and causes of gene mutations. Proc. 6th Int. Congr. Genet. 1, 213–252.

Priess, J. Schnabel, H. and Schnabel, R. (1987) The glp-1 locus and cellular interactions in early *C. elegans* embryos. Cell 51, 601–611.

Pulak, R. and Anderson, R. P. (1993) mRNA surveillance by the *Caenorhabditis elegans* smg genes. Genes Dev. 7, 1885–1897.

Robbins, J., Blondel, B. J., Gallahan, D. and Callahan, R. (1992) Mouse mammary tumor gene int-3: a member of the Notch gene family transforms mammary epithelial cells. J. Virol. 66, 2594–2599.

Rogaev, E. I. et al. (1995) Familial Alzheimer's disease in kindreds with missense mutations in a gene on chromosome 1 related to the Alzheimer's disease type 3 gene. Nature 376: 775–778.

Rushforth, A. M., Saari, B., and Anderson, R. P. (1993) Site-selected insertion of the transposon Tc1 into a *Caenorhabditis elegans* myosin light chain gene. Mol. Cell. Biol. 13, 902–910.

Sherrington, R. et al. *Nature* 375, 754–759 (1995).

Sigurdson, D. C., G. J. Spanier, and Herman, R. K. (1984) *Caenorhabditis elegans* deficiency mapping. Genetics 108: 331–345.

Stringham, E. G., Dixon, D. K., Jones, D. and Candido, E. P. M. (1992) Temporal and spatial expression patterns of the small heat shock (hsp 16) genes in transgenic *Caenorhabditis elegans*. Mol. Biol. Cell 3, 221–233.

Struhl, G., Fitzgerald, K. and Greenwald, I. *Cell* 64, 331–345 (1993).

Sundaram, M. V. and Greenwald, I. (1993) Genetic and phenotypic studies of hypomorphic lin-12 mutants of *C. elegans*. Genetics 135, 755–763.

Swiatek, P. J., Lindsell, C. E., Franco del Amo, F., Weintmaster, G. and Gridley, T. *Genes & Development* (1994).

Wilkinson, H. A., Fitzgerald, K. and Greenwald, I. *Cell* 79, 1187–1198 (1994).

Wilkinson, H. A. and Greenwald, I. (1995) Spatial And temporal Patterns of lin-12 expression during *C. elegans* hermaphrodite development. Genetics, in press.

Zwaal, R. R., Broeks, A., Vanmeurs, J., Groenen, J. T. M. and Plasterk, R. H. (1993) Target-selected gene inactivation in *Caenorhabditis elegans* by using a frozen transposon insertion mutant bank. Proc. Natl. Acad. Sci. (USA) 90, 7431–7435.

Third Series of Experiments

Ass ssm nt of Normal and Mutant Human Presenilin Function in *C. elegans*

Applicants provide evidence that normal human presenilins can substitute for *C. elegans* SEL-12 protein in functional assays in vivo. In addition, six familial Alzheimer's disease-linked mutant human presenilins were tested and found to have reduced ability to rescue the sel-12 mutant phenotype, suggesting that they have lower than normal presenilin activity. A human presenilin 1 deletion variant that fails to be proteolytically processed and a mutant SEL-12 protein that lacks the carboxy terminus display considerable activity in this assay, suggesting that neither presenilin proteolysis nor the carboxy terminus is absolutely required for normal presenilin function. Applicants also show that sel-12 is expressed in most neural and non-neural cell types in all developmental stages. The reduced activity of mutant presenilins together with as yet unknown gain-of-function properties may be a contributing factor in the development of Alzheimer's disease.

Genetic linkage studies have identified a number of genetic loci associated with familial Alzheimer's disease (1). Mutations in two genes, encoding the presenilins PS1 and PS2, are dominant and fully penetrant (1, 2, 3, 4, 5). PS1 and PS2 are related multipass transmembrane proteins that are about 67% identical in amino acid sequence. The presenilins are ubiquitously expressed (4, 5), and found in conjunction with intracellular membranes (6).

The normal function of presenilins, and the mechanism by which mutant presenilins cause Alzheimer's disease, are not yet known. The fact that more than thirty dominant, fully penetrant mutations in PS1 and PS2 are all missense mutations has suggested that Alzheimer's disease is associated with a gain-of-function activity of mutant proteins, although it remains formally possible that they partially lower activity of a dose-sensitive gene. Indeed, mutations may also have more than one effect on gene activity, and may have both gain-of-function and loss-of-function characteristics. Classical studies have indicated that gain-of-function mutations in principle fall into one of three classes: hypermorphic mutations, which elevate gene activity; antimorphic mutations, which reduce wild-type gene activity in trans (this category includes dominant-negative mutations); and neomorphic mutations, which create a novel activity (7). However, at the biochemical level, even the novel activity resulting from neomorphic mutations is related to the normal mechanism of gene function. For example, neomorphic mutations in the Drosophila awd gene appear to alter the substrate specificity of nucleoside diphosphate kinase as well as reduce activity for its normal substrate (8), and mutations that cause familial amyotropic lateral sclerosis affect different activities of the normal protein, increasing the level of peroxidase activity (9) while in some cases reducing superoxide dismutase activity (10). Thus, an understanding of the normal function of presenilins as well as the nature of the dominant mutations is crucial to elucidating the role of mutant presenilins in Alzheimer's disease.

Genetic studies in simple organisms offer a powerful approach to understanding the role of presenilins. A *C. elegans* gene, sel-12, encodes a protein that displays about 50% amino acid sequence identity to PS1 and PS2 (11). sel-12 was identified by reverting a phenotype caused by constitutive activation of LIN-12, a member of the LIN-12/Notch family of receptors [sel=suppressor/enhancer of lin-12]. Genetic analysis established that reducing or eliminating sel-12 activity reduces the activity of lin-12, and causes an egg-laying defective (Egl) phenotype. The Egl phenotype may be a direct consequence of reducing lin-12 activity (12) or an independent effect of reducing sel-12 activity. In this paper, applicants provide evidence that SEL-12 and the presenilins are functional homologs, and that studies in *C. elegans* will be directly applicable to issues of presenilin structure and function in humans.

Materials and Methods

General methods and mutations used. Methods for handling and culturing C. elegans have been described (13). The wild-type parent for all strains used was C. elegans var. Bristol strain N2 (13). sel-12(ar131) is described in ref. 11. All strains containing pLEX-based plasmids (see below) contained the smg1(r861) and unc-54(r293) mutations (14). smg-1 mutations stabilize mRNAs with long 3' untranslated regions (15), and unc-54(r293) is suppressed by smg-1I (r861) (14). pLEX-based constructs. The pLEX vector has been described previously (16). It contains a 15.1 kb genomic region encompassing the lin-12 gene, in which the normal translational start ATG was destroyed and replaced with a NotI site. cDNAs containing stop codons but lacking polyadenylation signals are inserted into the NotI site, and are efficiently expressed in a smg-1 background. The following cDNAs were inserted into pLEX for this study.

sel-12: The sel-12 cDNA is described in ref. 11 and, as described below, results in efficient rescue of a sel-12 mutant. Applicants note here that the C. elegans genome project has sequenced through the sel-12 region (R. Waterston et al., personal communication). By comparing the genomic sequence with that of the available sel-12 cDNA, applicants discovered that the cDNA has a frameshift mutation, beginning at codon 413, probably introduced by reverse transcription. This frameshift results in the substitution of 31 amino acids C-terminal to the frameshift mutation by 49 amino acids.

PS1: Full-length human PS1 cDNA and cDNA encoding the PS1 A246E-substitution were generated by RT-PCR of cytoplasmic RNA isolated from skin fibroblasts of a patient harboring the A246E mutation (NIA Cell Repository #AG06848B) using a sense primer, hAD3-ATG-Kpn (GGGGTACCATGACAGAGTTACCTGCAC, SEQ ID NO:10), and antisense primer, hAD3-R-3'UTR (CCGGGATCCATGGGATTCTAACCGC, SEQ ID NO:11). PCR products were digested with Asp718 and BamHI and ~1.4 kB hPS1cDNAs were gel purified and ligated to Bluescript KS+ vector (Stratagene, La Jolla, Calif.) previously digested with Asp718 and BamHI, to generate phPS1 and phPS1A246E. The cDNAs were sequenced in their entirety using a Sequenase kit (U.S. Biochemical Corp., Cleveland, Ohio).

To generate human PS1 cDNA encoding the M146L, H163R, L286V or C410Y substitutions (5), applicants used a four-way PCR strategy with two primer pairs and full-length PS1 cDNA as template. The inserts and junctions were sequenced using Sequenase (U.S. Biochemical Corp. (Cleveland, Ohio).

For M146L, primer pairs were hAD3-M146LF (GTCATTGTTGTCCTGACTATCCTCCTG, SEQ ID NO:12)/hAD3-R284 (GAGGAGTAAATGAGAGCTGG, SEQ ID NO:13) and hAD3-M146LR (CAGGAGGATAGTCAGGACAACAATGAC, SEQ ID NO:14/hAD3-237F (CAGGTGGTGGAGCAAGATG, SEQ ID NO:15). PCR products from each reaction were gel purified, combined and subject to a second round of PCR with primers hAD3-237F and hAD3-R284. The resulting product was digested with KasI and PflMI and an ~300 bp gel purified fragment was ligated to KasI/PflMI-digested phPS1 to generate phPS1M146L. For H163R, primer pairs were hAD3-H163RF (CTAGGTCATCCGTGCCTGGC, SEQ ID NO:16/hAD3-R284 and hAD3-H163RR (GCCAGGCACGGATGACCTAG, SEQ ID NO:17/hAD3-237F. PCR products from each reaction were gel purified, combined and subject to a second round of PCR with primers hAD3-237F and hAD3-R284. The resulting products were digested with KasI and PflMI and a gel-purified ~300 bp fragment was ligated to KasI/PflMI-digested phPS1 to generate phPS1H163R.

For L286V, primer pairs were hAD3-L286VF (CGCTTTTTCCAGCTGTCATTTACTCC, SEQ ID NO:18)/hAD3-RL-GST (CCGGAATTCTCAGGTTGTGTTCCAGTC, SEQ ID NO:19) and hAD3-L286VR (GGAGTAAATGACAGCTGGAAAAAGCG, SEQ ID NO:20/hAD3-F146 (GGATCCATTGTTGTCATGACTATC, SEQ ID NO:21). PCR products from each reaction were gel purified, combined and subject to a second round of PCR with primers hAD3-F146 and hAD3-RL-GST. The resulting products were digested with PflMI and BbsI and a gel purified ~480 bp fragment was ligated to PflMI/BbsI-digested phPS1 to generate phPS1L286V.

For C410Y, primer pairs were hAD3-C410YF (CAACCATAGCCTATTTCGTAGCC, SEQ ID NO:22/ LRT7 (GCCAGTGAATTGTAATAGGACTCACTATAGGGC, SEQ ID NO:23) and hAD3-C410YR (GGCTACGAAATAGGCTATGGTTG, SEQ ID NO:24)/ hAD3-243S (CCGGAATTCTGAATGGACTGCGTG, SEQ ID NO:25). PCR products from each reaction were gel purified, combined and subject to a second round of PCR with primers hAD3-243S and LRT7. The resulting products were digested with BbsI and BamHI and an ~300 bp fragment was gel purified and ligated to BbsI/BamHI-digested phPS1 to generate phPS1C410Y.

The strategy for generating cDNA encoding hPS1 lacking exon 9 (amino acids 290–319) was described previously (17).

PS2: Full-length cDNA encoding human PS2 was generated by RT-PCR of total human brain RNA using a sense primer, huAD4-ATGF (CCGGTACCAAGTGTTCGTGGTGCTTCC, SEQ ID NO:26) and antisense primer, hAD4-stopR (CCGTCTAGACCTCAGATGTAGAGCTGATG, SEQ ID NO:27). PCR products were digested with Asp718 and XbaI and ~1.4 kB hPS2 cDNA were gel isolated and ligated to a vector fragment from expression plasmid pCB6 (17) previously digested with Asp7,18 and XbaI to generate phPS2. The insert was sequenced in its entirety using a Sequenase kit (U.S. Biochemical Corp., Cleveland, Ohio).

Transgenic lines and rescue assays. Transgenic lines were established by microinjection of plasmid mixtures into the hermaphrodite germline to create extrachromosomal arrays (18). By accepted convention, "Ex" is used to represent extrachromosomal arrays, and "Is" to represent integrated arrays (which can be generated from extrachromosomal arrays; see below).

pLEX and derivatives were injected at 20 μg/ml, 2 μg/ml or other concentrations (data not shown) into recipient strains of genotype smg-1(r861) unc-54(r293); sel-12 (ar131) or smg-1(r861)unc-54(r293). pRF4, a plasmid containing the cloned dominant rol-6(su1006) gene (18) was used as a cotransformation marker and coinjected at a concentration of 100 μg/ml. F1 Roller progeny were picked, and F2 Roller progeny used to establish lines.

To assess rescue of sel-12(ar131), approximately 40 L4 Rol progeny from at least three independent lines generated in a smg-1(r861) unc-54(r293); sel-12 (ar131) background were picked individually and scored daily for the ability to lay eggs. Applicants note here that rescue assays were performed using sel-12(ar131), a strong partial loss-of-function allele of sel-12, because the strongest existing sel-12 mutation, sel-12(ar171), is somewhat suppressed by smg-1 (data not shown). sel-12(ar131) displays variable penetrance (see Table 4) and expressivity. About 10% of sel-12(ar131) hermaphrodites have normal egg-laying, while 90% of hermaphrodites bloat with retained eggs; some of these bloated hermaphrodites never lay eggs, whereas others lay eggs. However, the proportion of hermaphrodites that lay eggs normally appears to be reduced by the pLEX vector and/or the rol-6 cotransformation marker (see Table 4). Applicants scored hermaphrodites as "Egl+" only if they displayed robust egg-laying characteristic of wild-type hermaphrodites after two days as adults. However, applicants note that a greater proportion of hermaphrodites containing human wild-type and mutant presenilins displayed improved egg-laying after one day compared to control hermaphrodites (data not shown), indicating that the criterion of normal egg-laying after two days underestimates rescuing activity. The pLEX vector causes a low level of sterility, and sterile hermaphrodites were not scored.

TABLE 4

| transgene* | line | Egl+/total (%)† |
| --- | --- | --- |
| none | — | 3/44 (6.8) |
| pLEX | 1 | 1/71 (1.4) |
|  | 2 | 0/36 (0) |
|  | 3 | 1/40 (2.5) |
| SEL-12‡ | 1 | 36/39 (92.3) |
|  | 2 | 38/40 (95.0) |
|  | 3 | 40/40 (100) |
| PS1 | 1 | 30/44 (68.1) |
|  | 2 | 33/40 (83.0) |
|  | 3 | 32/40 (80.0) |
| PS2 | 1 | 26/39 (67.0) |
|  | 2 | 33/40 (83.0) |
|  | 3 | 32/40 (80.0) |
| PS1 M146L | 1 | 4/39 (10.3) |
|  | 2 | 6/37 (16.2) |
|  | 3 | 2/29 (6.9) |
| PS1 H163R | 1 | 12/38 (31.6) |
|  | 2 | 7/38 (18.4) |
|  | 3 | 23/38 (60.5) |
| PS1 A286E | 1 | 4/36 (11.1) |
|  | 2 | 5/39 (12.8) |
|  | 3 | 3/39 (7.7) |
| PS1 L266V | 1 | 11/38 (28.9) |
|  | 2 | 6/38 (15.8) |
|  | 3 | 9/38 (23.7) |
| PS1 C410Y | 1 | 7/36 (19.4) |
|  | 2 | 2/35 (5.7) |
|  | 3 | 7/38 (18.4) |
| PS1 ΔE9 | 1 | 26/39 (66.7) |
|  | 2 | 28/38 (73.7) |
|  | 3 | 17/27 (63.0) |

Rescue of the sel-12 egg-laying defective (Egl) and abnormal vulva phenotypes by normal and mutant human presenilins. The data is shown for transgenic lines generated by injecting the construct being tested at a concentration of 20 μg/ml. See Methods for details about generating and scoring transgenic lines.
*Most PS1 mutations that cause Alzheimer's disease affect amino acids that are identical in SEL-12. The amino termini of PS1, PS2 and SEL-12 are not well conserved and are of different lengths. Therefore, for the mutations used here, the amino acid corresponding to M146 in PS1 is M115 in SEL-12; PS1 H163 is SEL-12 H132; PS1 A246 is SEL-12 V216; PS1 L286 is SEL-12 L255; PS1 C410 is SEL-12 C384. The ΔE9 mutation inhibits cleavage of PS1 (17); applicants note that SEL-12 is cleaved in a comparable position (Li and Greenwald, submitted).
†Egl+ signifies robust egg-laying characteristic of wild-type hermaphrodites after two days as adults. This criterion is the most stringent applicants could apply, and underestimates the degree of rescuing activity (see Materials and Methods).
‡Note that the sel-12 cDNA used (11) has a frameshift mutation, beginning at codon 413, resulting in the substitution of 31 amino acids C-terminal to the frameshift mutation by 49 amino acids (see Materials and Methods). See Materials and Methods for details about the human presenilin cDNAs.

Transgenic lines and β-galactosidase staining. pIB1Z17 [sel-12::lacZ] was made as follows: A unique BamHI site was inserted using the polymerase chain reaction at the second amino acid of a sel-12 rescuing genomic fragment containing 2.8 kb of 5' flanking region. A lacZ gene encoding a β-galactosidase protein containing a nuclear localization signal was excised from plasmid pPD16.43 (19) and inserted in frame into the BamHI site to generate the plasmid pIB1Z17. The predicted transcript contains an abnormally long 3' untranslated region, consisting of the sel-12 coding and 3' untranslated region, and is expected to be stabilized in a smg-1 background (15). pIB1Z17 was injected at a concentration of 10 μg/ml into smg-1 unc-54 hermaphrodites. 9 independent lines containing extrachromosomal arrays were established. 4 independent attached lines were generated (using the method of C. Kari, A. Fire and R. K. Herman, personal communication) from one of the extrachromosomal arrays. All integrated and 7 of the 9 extrachromosomal arrays displayed staining; all staining lines had similar expression patterns, but some lines displayed more variability in intensity or penetrance of staining. The analysis described in this paper was performed using the attached array arIs17.

Mixed stage populations were grown at 25°, fixed using an acetone fixation protocol (20) and stained for β-galactosidase activity overnight at room temperature. Stained nuclei were identified based on their size, shape and position (21,22). Counterstaining with 4,6-diamidino-2 phenylindole (DAPI) allowed visualization of all nuclei in the animal by fluorescence microscopy, facilitating the unambiguous identification of stained nuclei. Pictures of the staining pattern were taken at 1000× using TMAX400 (Kodak) film.

Results

A presenilin functional assay. There are currently no biochemical assays for presenilins, so there has been no direct assay for the effects of mutations on presenilin function. The high level of similarity between SEL-12, PS1 and PS2 suggested that the ability to rescue the distinctive egg-laying defective (Egl) phenotype caused by mutations that reduce or eliminate sel-12 activity (11) could serve as an assay for presenilin function. The pLEX vector (16), which places inserted cDNAs under the control of lin-12 regulatory sequences, can direct sufficient expression of a full-length sel-12 cDNA (11; see Materials and Methods) to rescue the sel-12(ar131) Egl phenotype (Table 4). Applicants describe below how applicants have used this assay to evaluate the activity of normal and mutant human presenilins.

Rescue is assessed in transgenic lines, which are created by the microinjection of plasmid DNA into the hermaphrodite germline. This procedure generates extrachromosomal arrays, and there is some inherent variability in expression from different arrays, in part due to different numbers of copies of plasmid incorporated into the array (18). However, variability can be controlled for by examining multiple independent lines for each construct. Furthermore, arrays generated at the same concentration of injected DNA are likely to have comparable numbers of plasmid copies and therefore comparable levels of transgene expression (18). In all of the experiments described below, applicants have examined three independent lines for each construct, and compare the results for lines generated at the same concentration of injected DNA.

Rescue of a sel-12 mutant by wild-type PS1 and PS2. Applicants have assessed the ability of wild-type human PS1 or PS2 cDNAs to rescue the Egl defect of sel-12(ar131) hermaphrodites (Table 4). Applicants found that the human proteins can efficiently substitute for SEL-12 in this assay, despite the vast evolutionary distance between nematodes and humans. The human proteins seem to be slightly less efficient than the C. elegans protein, but this small difference might in principle result from inefficient translation of human presenilin RNA due to the different codon usage between C. elegans and humans, so that less presenilin protein may be produced even if a comparable level of mRNA is expressed from the extrachromosomal arrays. The dramatic increase in sel-12 activity when PS1 or PS2 is expressed using lin-12 regulatory sequences, even at a relatively low concentration of injected DNA (Table 5), suggests that the human proteins are substituting for *C. elegans* SEL-12. An alternative interpretation is that the human protein functions in this assay by stabilizing the mutant endogenous SEL-12(ar131) protein. However, this interpretation seems less likely in view of the efficient rescue; furthermore, a corrective interaction of this sort would imply that a SEL-12 and PS1 or PS2 complex is functional, which in itself would be evidence for functional similarity of the *C. elegans* and human proteins.

Activity of PS1 point mutants. Applicants expressed five different human mutant PS1 proteins, each containing a single amino acid alteration that causes Alzheimer's disease, and found that most displayed reduced ability to rescue sel-12(ar131) relative to wild-type PS1 (Table 4). These data suggest that the mutations that cause Alzheimer's disease may reduce but not eliminate normal presenilin activity. The variable loss of extrachromosomal arrays confounds any determination of steady-state protein levels, so applicants do not know if the apparently lower activity of mutant presenilins results from reduced protein stability or reduced function.

Activity of PS1 ΔE9. PS1 is subject to endoproteolysis in vivo, and the PS1 ΔE9 mutant fails to be cleaved (17). Applicants have found that the human mutant PS1 ΔE9 retains a high level of activity, when arrays are formed at the concentration of 20 µg/ml of injected DNA (Table 4). Since arrays generated at a concentration of 20 µg/ml of injected DNA are likely to contain many plasmid copies, which might mask a small difference in relative activity of PS1 and PS1 ΔE9, applicants generated arrays at the concentration of 2 µg/ml of injected DNA. At this concentration of injected DNA, the number of copies of plasmid present in the arrays should be reduced roughly tenfold (Mello et al., 1991). At this lower concentration, PS1 ΔE9 has reduced ability to rescue sel-12(ar131) as compared to wild-type PS1 (Table 5), suggesting that PS1 ΔE9, like the PS1 missense mutations, has reduced activity.

TABLE 5

| transgene | line | Eg1+/total (%)* |
|---|---|---|
| pLEX | 1 | 1/35 (2.9) |
|  | 2 | 0/38 (0) |
| SEL-12‡ | 1 | 38/40 (95.0) |
|  | 2 | 40/40 (100) |
|  | 3 | 8/20 (40.0) |
| PS1 | 1 | 8/31 (25.8) |
|  | 2 | 36/41 (87.8) |
|  | 3 | 34/37 (92.0) |
|  | 4 | 33/40 (91.9) |
|  | 5 | 34/40 (85.0) |
| PS1 ΔE9 | 1 | 6/37 (16.2) |
|  | 2 | 5/39 (12.8) |
|  | 3 | 5/37 (13.5) |
|  | 4 | 14/41 (34.1) |
|  | 5 | 1/40 (2.5) |

Rescue of the sel-12 Eg1 phenotype by PS1 and PS1 ΔE9 expressed from arrays formed at a concentration of 2 µg/ml. At 2 µg/ml of injected DNA, expression from arrays or representation of the plasmid in the arrays may be reduced, accounting for the reduced activity of SEL-12 (transgenic line 3) and PS1 (transgenic line 1) compared to arrays generated at 20 µg/ml (Table 4).
*Eg1+, see Table 4 legend and Materials and Methods.
‡ see Table 4 legend and Materials and Methods for comments about the sel-12 cDNA used.

Examination of PS1 mutant transgenes in a sel-12(+) background. In an attempt to reveal gain-of-function activity, applicants assayed the ability of transgenes encoding mutant presenilins to cause phenotypes in a sel-12(+) background. Applicants saw no evidence for gain-of-function activity in this assay, as measured by the failure to obtain highly penetrant Egl or vulval abnormalities associated with abnormal sel-12 or lin-12 activity (data not shown). However, intrinsic limitations of the pLEX expression system (see Materials and Methods) may have masked moderate changes in sel-12 or lin-12 activity, so a definitive assessment of the gain-of-function activity of mutant presenilins in *C. elegans* will not be possible until other expression systems or strategies are developed.

sel-12 is widely expressed in neural and non-neural cells. Applicants have examined the expression pattern of transgenic lines carrying a sel-12::lacZ reporter gene (see Materials and Methods). Using this reporter gene, applicants have found that sel-12, like human presenilins (4, 5), is widely expressed in neural as well as non-neural cells (FIG. 3). Staining was seen in most cell types at all developmental stages from embryo to adult, with the notable exception of the intestine.

Discussion

Sequence analysis revealed that SEL-12 is similar to human presenilins (11). Here, applicants have provided experimental evidence that SEL-12 is a bona fide presenilin, since it may be functionally replaced by either of the two human presenilins. Applicants have also shown that sel-12 is widely expressed in most neural and non-neural tissues of developing animals and adults. Furthermore, SEL-12 and PS1 also appear to have similar membrane topology (Doan et al., submitted; L1 and Greenwald, submitted). These striking parallels between *C. elegans* and human presenilins suggest that studies of SEL-12 in *C. elegans* will bear directly on fundamental issues of presenilin structure and function. In the absence of any description of proteins similar to presenilins in single-celled organisms, including *Saccharomyces cerevisiae*, it appears that *C. elegans* is the simplest practical system for studying issues relevant to the biology of presenilins in vivo.

Since PS1 and PS2 appear to be similar in their ability to substitute for SEL-12, they may also have overlapping functions in mammals. As a consequence, studies of normal and mutant PS1 proteins should be directly applicable to PS2, and vice versa. Furthermore, since PS1 and PS2 have broad and overlapping expression patterns (4, 5), the phenotype of mutants homozygous for null alleles of individual mouse presenilin genes may be less severe than the phenotype of double mutants, since there may be functional redundancy where the expression patterns overlap.

The rescue experiments also provide an indication that two regions of the presenilins are not essential for normal function. First, a SEL-12 protein lacking the last 31 amino acids is highly functional (see Table 4), suggesting that the C terminus is dispensable for SEL-12 function. Second, the PS1 ΔE9 protein, which 30 amino acids and fails to be proteolytically cleaved (17), retains considerable activity, suggesting that neither the deleted region nor cleavage is a prerequisite for presenilin activity. Applicants note that the rescue experiments do not address the possibility that the various mutations applicants tested have gain-of-function activity. Although the nature of the hypothetical gain-of-function activity of mutant presenilins is not clear, the mutant presenilins appear to increase the extracellular concentration of Aβ1-42(43) (ref. 23; Borchelt et al., submitted), and hence may cause Alzheimer's disease by fostering Aβ deposition.

By expressing human genes in *C. elegans*, applicants have obtained evidence that six different presenilin mutations that cause early-onset Alzheimer's disease lower normal presenilin activity. Hypomorphic characteristics were manifested as reduced ability to rescue a C. elegans mutant defective in sel-12 presenilin function. In the absence of any other assays for normal presenilin function, this information may be useful in considering the pathogenesis of Alzheimer's disease, and the development of mammalian models for the disease. It is possible that reduced presenilin activity may contribute to the development of Alzheimer's disease, either directly or in conjunction with an as yet unknown gain-of-function activity associated with mutant presenilins.

Gain-of-function Activity of sel-12(Alz) Transgenes

The applicants have modified the C. elegans sel-12 gene to encode mutant proteins corresponding to PS1 mutants that cause Alzheimer's disease in people. Transgenic C. elegans lines containing these sel-12(Alz) genes have a novel gain-of-function activity (manifested as an egg-laying constitutive ($Egl^c$) phenotype), which may be mechanistically related to a gain-of-function activity that is presumed to underlie the development of Alzheimer's disease. The penetrance of the $Egl^c$ phenotype is enhanced in a sel-12(ar171) background. An $Egl^c$ phenotype has been known to be associated with stimulation of a G protein coupled serotonergic neural pathway in C. elegans (Segalat et al., 1995; Mendel et al., 1995: Kopelle and Horvitz, 1996). The applicants are currently exploring the effects of sel-12(Alz) mutations on other neural signalling pathways that involve G protein coupled 7 transmembrane domain receptors, and neural signalling pathways that may involve other kinds of signal transduction pathway.

sel-12 Mutant

| transgene | line | $Egl^c/Egl^+$ (%) |
|---|---|---|
| + | 1 | 0/37 (0) |
|   | 2 | 1/38 (2.6) |
|   | 3 | 0/38 (0) |
| H132R | 1 | 2/38 (5.3) |
|   | 2 | 5/36 (13.9) |
|   | 3 | 2/39 (5.1) |
| V216E | 1 | 2/31 (6.5) |
| G363A | 1 | 11/31 (35.5) |
|   | 2 | 13/40 (32.5) |
|   | 3 | 16/40 (40.0) |

Data shown are for transgenes in a sel-12(ar171) genetic background.

It may be that drugs that reduce serotonergic signalling or other signalling pathways that the applicants will test will suppress sel-12(Alz) gain-of-function phenotypes, thereby suggesting potential prophylactic or therapeutic treatments, particularly if these signalling pathways or related pathways are shown to be affected in Alzheimer's disease. It may also be that the effect of drugs that reduce the gain-of-function activity of mutant presenilins will be potentiated by drugs that increase the normal activity of presenilins.

spr Genes: Suppressors of sel-12(ar171)

sel-12(ar171) hermaphrodites are egg-laying defective (Egl). The applicants have identified more than fifty extragenic suppressors of the Egl defect of sel-12(ar171) after EMS mutagenesis. The applicants have thus far assigned seven of the semidominant suppressor mutations to four new genes, named spr-1 through spr-4 [spr stands for suppressor of presenilin]. Two recessive suppressors probably define two additional spr genes. The remaining mutations are currently being analyzed and will be assigned to genes based on map position, genetic properties, and for recessive mutations, by complementation tests.

Gene dosage studies suggest that spr-1V mutations are hypermorphic, and that excess copies of the wild-type locus suppress sel-12(ar171). The applicants are currently performing equivalent gene dosage studies with spr-2 II, which has been mapped to a 0.25 map unit interval corresponding to about 200 kb, and with spr-3 III. Meanwhile, assuming that the spr-2 mutation is hypermorphic and that excess copies of the wild-type locus will suppress sel-12(ar171), the applicants have embarked on cloning spr-2 by injecting pools of cosmid clones from the spr-2 region into sel-12 (ar172), and preliminary data suggest that this strategy will be successful The identification of suppressor mutations is a classical genetic tool used to identify other components of biochemical pathways. Extragenic suppressor mutations may identify new genes that are involved in presenilin-mediated processes, or reveal a functional connection between a previously known gene and presenilin function. Genetic and molecular characterization of these "suppressor genes" in C. elegans will reveal the nature of their interactions with sel-12 and lin-12. This analysis is directly relevant to Alzheimer's disease because the biochemical function of the presenilins is not known, so that a potential outcome of analyzing a suppressor gene would be an insight into the biochemistry of presenilin-mediated processes. If the suppressor gene has a known biochemical activity (based on sequence analysis), then, combined with the results of genetic analysis, the information will potentially be useful for the design and testing of therapeutic agents in both C. elegans and mammalian models, and ultimately for people. Furthermore, human homologs of the suppressor genes themselves may be useful diagnostic reagents, perhaps for the analysis of other inherited forms of Alzheimer's disease or for sporadic forms.

Topology and Structure/Function Studies

The applicants have obtained evidence that SEL-12 presenilin contains 8 transmembrane domains (Li and Greenwald, submitted), and that certain regions of presenilins are dispensable for normal presenilin activity (Levitan et al., submitted). The applicants are continuing to do structure/function studies, by engineering mutant sel-12 transgenes and assessing them in vivo in transgenic C. elegans_lines for the ability to rescue defects associated with reducing sel-12 activity and for gain-of-function activity.

Further structure/function studies in C. elegans may clarify the functions of domains of presenilin and be useful in conjunction with ultrastructural studies for rational drug design.

Gene and Allele Specificity Studies

The applicants have been making double mutants between sel-12(ar171) and mutations in other secreted or transmembrane proteins. Thus far, a genetic interaction has been seen with a mutation in a TGF-β receptor gene, daf-1. This result suggests that sel-12 may interact with genes other than lin-12 and glp-1.

| genotype | % Daf |
|---|---|
| daf-1(m213) | 13% |
| daf-1(m213); sel-12(ar171) | 98% |

Interactions of this sort may enable the design of other suppressor/enhancer screens.

Other C. elegans Presenilin Genes

The applicants regularly search the C. elegans genomic sequence database for sequences related to sel-12. Recently, a predicted protein encoded by a sequence present on cosmid C18E3 was found to have significant similarity to SEL-12. The applicants will test any potentially related sequences for the ability to complement sel-12(ar131) as described in Levitan et al. (submitted). Any sequences that behave like SEL-12/presenilins by this functional assay will be studied further.

Other *C. elegans* presenilins can be studied in the same way as sel-12 in order to gain insights into presenilin structure and function, and Alzheimer's disease. The applicants will identify mutations in the new presenilins, identify suppressors of these new presenilin mutants, perform structure/function studies, and look for genetic interactions with lin-12, glp-1 and other genes.

References of Third Series of Experiments

1. Schellenberg, G. D. (1995) *Proc. Natl. Acad. Sci.* (*USA*) 92, 8552–8559.
2. Clark, R. F., et al. (1995) *Nature Genet.* 11, 219–222.
3. Levy-Lahad, E., et al. (1995) *Science* 269, 973–977.
4. Rogaev, E. I., et al. (1995) *Nature* 376, 775–778.
5. Sherrington, R., et al. (1995) *Nature* 375, 754–760.
6. Kovacs, D. M., Fausett, H. J., Page, K. J., Kim, T.-W., Moir, R. D., Merriam, D. E., Hollister, R. D., Hallmark, O. G., Mancini, R., Felsenstein, K. M., Hyman, B. T., Tanzi, R. E., Wasco, W. (1996) *Nature Medicine* 2, 224–229.
7. Muller, H. J. (1932) *Proc. Intl. Congr. Genet.* 6, 213–252.
8. Timmons, L., Xu, J., Hersperger, G., Deng, X. F., Shearn, A. (1995) *J. Biol. Chem.* 23021–23030.
9. Wiedau-Pazos, et al. (1996) *Science* 271, 515–518.
10. Borchelt D. R., Lee, M. K., Slunt H. S., Guarnieri M., Xu Z. S., Wong P. C., Brown R. H. Jr., Price D. L., Sisodia S. S., Cleveland, D. W. (1994) *Proc. Natl. Acad. Sci.* (*USA*) 91, 8292–8296.
11. Levitan, D., Greenwald, I. (1995) *Nature* 377, 351–354.
12. Sundaram, M., Greenwald, I. (1993a) *Genetics* 135, 755–763.
13. Brenner, S. (1974) *Genetics* 77, 71–94.
14. Hodgkin, J., Papp, A., Pulak, R., Ambros, V., Anderson, P. (1989) *Genetics* 123, 301–313.
15. Pulak, R., Anderson, P. (1993) *Genes Dev.* 7, 1885–1897.
16. Struhl, G., Fitzgerald, K., Greenwald, I. (1993) *Cell* 74, 331–345.
17. Thinakaran, G., Borchelt, D. R., Lee, M. K., Slunt, H. H., Spitzer, L., Kim, G., Ratovitsky, T., Davenport, F., Nordstedt, C., Seeger, M., Hardy, J., Levey, A. I., Gandy, S. E., Jenkins, N. A., Copeland, N. G., Price, D. L., Sisodia, S. S. (1996) *Neuron* 17, 181–190.
18. Mello, C. C., Kramer, J. M., Stinchcomb, D. T., Ambros, V. A. (1991) *EMBO Journal* 10, 3959–3970.
19. Fire, A., Harrison, S. W., Dixon, D. (1990) *Gene* 93, 189–198.
20. Fire, A. (1993) *Genet. Anal. Tech. Appl.* 151–158.
21. Sulston, J., Horvitz, H. R. (1977) *Developmental Biology* 56, 110–156.
22. Kimble, J., Hirsh, D. (1979) *Developmental Biology* 81, 208–221.
23. Scheuner, D., et al. (1996) *Nature Medicine* 2, 864–870.

What is claimed is:

1. An isolated polynucleotide encoding a SEL-12, whose amino acid sequence comprises SEQ ID NO:1.

2. An isolated polynucleotide encoding SEL-12 having a mutation therein, consisting of an amino acid substitution selected from the group consisting of: a leucine at position 115, an arginine at position 132, a glutamic acid at position 215, a tyrosine at position 387, or an isoleucine at position 104, which position numbers correspond to the position numbers of SEQ ID NO:1.

3. An isolated polynucleotide encoding SEL-12 having therein a mutation selected from the group consisting of a valine substitution at position 229, 254, 255, 371, or 204, which position numbers correspond to the position numbers of SEQ ID NO:1.

4. The polynucleotide of claim 2 or 3, wherein the mutation causes a reduction or elimination of SEL-12 activity.

5. An isolated polynucleotide of claim 1, 2, or 3 wherein said polynucleotide is DNA.

6. An isolated polynucleotide of claim 1, 2, or 3 wherein said polynucleotide is cDNA.

7. A vector which comprises the polynucleotide of claim 1, 2 or 3.

8. The vector of claim 7, wherein the polynucleotide is operatively linked to a promoter of RNA transcription.

9. The vector of claim 7, wherein the vector is a plasmid.

10. The plasmid designated pMX8, deposited with the American Type Culture Collection under Designation No. 97278.

11. The plasmid designated p1-1E, deposited with the, American Type Culture Collection under Designation No. 97279.

12. A host cell-vector combination system for the production of a SEL-12 protein which comprises the vector of claim 7 and a suitable host cell.

13. The host-cell vector combination of claim 12, wherein the suitable host cell is a bacterial cell, an insect cell, a plant cell or a mammalian cell.

* * * * *

SEQUENCE LISTING

```
<160> NUMBER OF SEQ ID NOS: 27

<210> SEQ ID NO 1
<211> LENGTH: 461
<212> TYPE: PRT
<213> ORGANISM: C. elegans
<220> FEATURE:
<221> NAME/KEY: misc_feature
<223> OTHER INFORMATION: Fig. 1A

<400> SEQUENCE: 1

Met Pro Ser Thr Arg Arg Gln Gln Glu Gly Gly Gly Ala Asp Ala Glu
1               5                   10                  15

Thr His Thr Val Tyr Gly Thr Asn Leu Ile Thr Asn Arg Asn Ser Gln
            20                  25                  30

Glu Asp Glu Asn Val Val Glu Glu Ala Glu Leu Lys Tyr Gly Ala Ser
        35                  40                  45

His Val Ile His Leu Phe Val Pro Val Ser Leu Cys Met Ala Leu Val
    50                  55                  60

Val Phe Thr Met Asn Thr Ile Thr Phe Tyr Ser Gln Asn Asn Gly Arg
65                  70                  75                  80

His Leu Leu Ser His Pro Phe Val Arg Glu Thr Asp Ser Ile Val Glu
                85                  90                  95

Lys Gly Leu Met Ser Leu Gly Asn Ala Leu Val Met Leu Cys Val Val
            100                 105                 110

Val Leu Met Thr Val Leu Leu Ile Val Phe Tyr Lys Tyr Lys Phe Tyr
        115                 120                 125

Lys Leu Ile His Gly Trp Leu Ile Val Ser Ser Phe Leu Leu Leu Phe
    130                 135                 140
```

```
Leu Phe Thr Thr Ile Tyr Val Gln Glu Val Leu Lys Ser Phe Asp Val
145                 150                 155                 160

Ser Pro Ser Ala Leu Leu Val Leu Phe Gly Leu Gly Asn Tyr Gly Val
                165                 170                 175

Leu Gly Met Met Cys Ile His Trp Lys Gly Pro Leu Arg Leu Gln Gln
                180                 185                 190

Phe Tyr Leu Ile Thr Met Ser Ala Leu Met Ala Leu Val Phe Ile Lys
                195                 200                 205

Tyr Leu Pro Glu Trp Thr Val Trp Phe Val Leu Phe Val Ile Ser Val
210                 215                 220

Trp Asp Leu Val Ala Val Leu Thr Pro Lys Gly Pro Leu Arg Tyr Leu
225                 230                 235                 240

Val Glu Thr Ala Gln Glu Arg Asn Glu Pro Ile Phe Pro Ala Leu Ile
                245                 250                 255

Tyr Ser Ser Gly Val Ile Tyr Pro Tyr Val Leu Val Thr Ala Val Glu
                260                 265                 270

Asn Thr Thr Asp Pro Arg Glu Pro Thr Ser Ser Asp Ser Asn Thr Ser
                275                 280                 285

Thr Ala Phe Pro Gly Glu Ala Ser Cys Ser Ser Glu Thr Pro Lys Arg
                290                 295                 300

Pro Lys Val Lys Arg Ile Pro Gln Lys Val Gln Ile Glu Ser Asn Thr
305                 310                 315                 320

Thr Ala Ser Thr Thr Gln Asn Ser Gly Val Arg Val Glu Arg Glu Leu
                325                 330                 335

Ala Ala Glu Arg Pro Thr Val Gln Asp Ala Asn Phe His Arg His Glu
                340                 345                 350

Glu Glu Glu Arg Gly Val Lys Leu Gly Leu Gly Asp Phe Ile Phe Tyr
                355                 360                 365

Ser Val Leu Leu Gly Lys Ala Ser Ser Tyr Phe Asp Trp Asn Thr Thr
370                 375                 380

Ile Ala Cys Tyr Val Ala Ile Leu Ile Gly Leu Cys Phe Thr Leu Val
385                 390                 395                 400

Leu Leu Ala Val Phe Lys Arg Ala Leu Pro Ala Leu Gln Phe Pro Phe
                405                 410                 415

Ser Pro Asp Ser Phe Phe Thr Phe Val Pro Ala Gly Ser Ser Pro His
                420                 425                 430

Leu Leu His Lys Ser Leu Lys Ser Val Tyr Tyr Ile Asn Ser Leu Phe
                435                 440                 445

Leu Pro Phe Leu Cys Ile Ile Asn Phe Ser Ile Ile Ser
    450                 455                 460

<210> SEQ ID NO 2
<211> LENGTH: 467
<212> TYPE: PRT
<213> ORGANISM: human
<220> FEATURE:
<221> NAME/KEY: misc_feature
<223> OTHER INFORMATION: Fig. 2A S182

<400> SEQUENCE: 2

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
                20                  25                  30

Arg Glu Arg Gln Glu His Asn Asp Arg Arg Ser Leu Gly His Pro Glu
```

-continued

```
                35                  40                  45
Pro Leu Ser Asn Gly Arg Pro Gln Gly Asn Ser Arg Gln Val Val Glu
             50                  55                  60

Gln Asp Glu Glu Asp Glu Glu Leu Thr Leu Lys Tyr Gly Ala Lys
 65                  70                  75                  80

His Val Ile Met Leu Phe Val Pro Val Thr Leu Cys Met Val Val
                 85                  90                  95

Val Ala Thr Ile Lys Ser Val Ser Phe Tyr Thr Arg Lys Asp Gly Gln
                100                 105                 110

Leu Ile Tyr Thr Pro Phe Thr Glu Asp Thr Glu Thr Val Gly Gln Arg
            115                 120                 125

Ala Leu His Ser Ile Leu Asn Ala Ala Ile Met Ile Ser Val Ile Val
130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
                180                 185                 190

Val Asp Tyr Val Thr Val Ala Leu Leu Ile Trp Asn Phe Gly Val Val
            195                 200                 205

Gly Met Ile Ser Ile His Trp Lys Gly Pro Leu Arg Leu Gln Gln Ala
            210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
                260                 265                 270

Glu Thr Ala Gln Glu Arg Asn Glu Thr Leu Phe Pro Ala Leu Ile Tyr
            275                 280                 285

Ser Ser Thr Met Val Trp Leu Val Asn Met Ala Glu Gly Asp Pro Glu
290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
            355                 360                 365

Leu Ala Gly Glu Asp Pro Glu Glu Arg Gly Val Lys Leu Gly Leu Gly
            370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Ala Ile Phe Lys Lys Ala Leu
                420                 425                 430

Pro Ala Leu Pro Ile Ser Ile Thr Phe Gly Leu Val Phe Tyr Phe Ala
            435                 440                 445

Thr Asp Tyr Leu Val Gln Pro Phe Met Asp Gln Leu Ala Phe His Gln
450                 455                 460
```

Phe Tyr Ile
465

<210> SEQ ID NO 3
<211> LENGTH: 157
<212> TYPE: PRT
<213> ORGANISM: C. elegans
<220> FEATURE:
<221> NAME/KEY: MISC_FEATURE
<222> LOCATION: (11)..(11)
<223> OTHER INFORMATION: unknown amino acid

<400> SEQUENCE: 3

Glu Gly Lys Ser Pro Ser Asn Thr Glu Arg Xaa Val Ile Met Leu Phe
1               5                   10                  15

Val Pro Val Thr Leu Cys Met Ile Val Val Ala Thr Ile Lys Ser
            20                  25                  30

Val Arg Phe Tyr Thr Glu Lys Asn Gly Gln Leu Ile Tyr Thr Pro Phe
            35                  40                  45

Thr Glu Asp Thr Pro Ser Val Gly Gln Arg Leu Leu Asn Ser Val Leu
        50                  55                  60

Asn Thr Leu Ile Met Ile Ser Val Ile Val Val Met Thr Ile Phe Leu
65                  70                  75                  80

Val Val Leu Tyr Lys Tyr Arg Cys Tyr Lys Phe Ile His Gly Trp Leu
                85                  90                  95

Ile Met Ser Ser Leu Met Leu Leu Phe Leu Thr Tyr Ile Tyr Leu
            100                 105                 110

Gly Glu Val Leu Lys Thr Tyr Asn Val Ala Met Asp Tyr Pro Thr Leu
            115                 120                 125

Leu Leu Thr Val Trp Glu Leu Arg Gly Ser Gly His Gly Val His Pro
        130                 135                 140

Leu Glu Gly Ala Phe Gly Ala Ala Glu Ala Tyr Leu Ser
145                 150                 155

<210> SEQ ID NO 4
<211> LENGTH: 465
<212> TYPE: PRT
<213> ORGANISM: C. elegans
<220> FEATURE:
<221> NAME/KEY: misc_feature
<223> OTHER INFORMATION: Fig. 2A SPE-4

<400> SEQUENCE: 4

Met Asp Thr Leu Arg Ser Ile Ser Ser Glu Leu Val Arg Ser Ser Gln
1               5                   10                  15

Leu Arg Trp Thr Leu Phe Ser Val Ile Ala Asn Met Ser Leu Thr Leu
            20                  25                  30

Ser Ile Trp Ile Gly Val Tyr Asn Met Glu Val Asn Ser Glu Leu Ser
            35                  40                  45

Lys Thr Tyr Phe Leu Asp Pro Ser Phe Glu Gln Thr Thr Gly Asn Leu
        50                  55                  60

Leu Leu Asp Gly Phe Ile Asn Gly Val Gly Thr Ile Leu Val Leu Gly
65                  70                  75                  80

Cys Val Ser Phe Ile Met Leu Ala Phe Val Leu Phe Asp Phe Arg Arg
                85                  90                  95

Ile Val Lys Ala Trp Leu Thr Leu Ser Cys Leu Leu Ile Leu Phe Gly
            100                 105                 110

Val Ser Ala Gln Thr Leu His Asp Met Phe Ser Gln Val Phe Asp Gln

```
            115                 120                 125
Asp Asp Asn Asn Gln Tyr Tyr Met Thr Ile Val Leu Ile Val Val Pro
    130                 135                 140

Thr Val Val Tyr Gly Phe Gly Gly Ile Tyr Ala Phe Phe Ser Asn Ser
145                 150                 155                 160

Ser Leu Ile Leu His Gln Ile Phe Val Val Thr Asn Cys Ser Leu Ile
                165                 170                 175

Ser Val Phe Tyr Leu Arg Val Phe Pro Ser Lys Thr Thr Trp Phe Val
            180                 185                 190

Leu Trp Ile Val Leu Phe Trp Asp Leu Phe Ala Val Leu Ala Pro Met
        195                 200                 205

Gly Pro Leu Lys Lys Val Gln Glu Lys Ala Ser Asp Tyr Ser Lys Cys
    210                 215                 220

Val Leu Asn Leu Ile Met Phe Ser Ala Asn Glu Lys Arg Leu Thr Ala
225                 230                 235                 240

Gly Ser Asn Gln Glu Glu Thr Asn Glu Gly Glu Ser Thr Ile Arg
                245                 250                 255

Arg Thr Val Lys Gln Thr Ile Glu Tyr Tyr Thr Lys Arg Glu Ala Gln
            260                 265                 270

Asp Asp Glu Phe Tyr Gln Lys Ile Arg Gln Arg Ala Ala Ile Asn
        275                 280                 285

Pro Asp Ser Val Pro Thr Glu His Ser Pro Leu Val Glu Ala Glu Pro
    290                 295                 300

Ser Pro Ile Glu Leu Lys Glu Lys Asn Ser Thr Glu Leu Ser Asp
305                 310                 315                 320

Asp Glu Ser Asp Thr Ser Glu Thr Ser Ser Gly Ser Ser Asn Leu Ser
                325                 330                 335

Ser Ser Asp Ser Ser Thr Thr Val Ser Thr Ser Asp Ile Ser Thr Ala
            340                 345                 350

Glu Glu Cys Asp Gln Lys Glu Trp Asp Leu Val Ser Asn Ser Leu
        355                 360                 365

Pro Asn Asn Asp Lys Arg Pro Ala Thr Ala Ala Asp Ala Leu Asn Asp
    370                 375                 380

Gly Glu Val Leu Arg Leu Gly Phe Gly Asp Phe Val Phe Tyr Ser Leu
385                 390                 395                 400

Leu Ile Gly Gln Ala Ala Ala Ser Gly Cys Pro Phe Ala Val Ile Ser
                405                 410                 415

Ala Ala Leu Gly Ile Leu Phe Gly Leu Val Val Thr Leu Thr Val Phe
            420                 425                 430

Ser Thr Glu Glu Ser Thr Thr Pro Ala Leu Pro Leu Pro Val Ile Cys
        435                 440                 445

Gly Thr Phe Cys Tyr Phe Ser Ser Met Phe Phe Trp Glu Gln Leu Tyr
    450                 455                 460

Gly
465

<210> SEQ ID NO 5
<211> LENGTH: 1500
<212> TYPE: DNA
<213> ORGANISM: C. elegans
<220> FEATURE:
<221> NAME/KEY: misc_feature
<223> OTHER INFORMATION: Fig. 1A

<400> SEQUENCE: 5
```

```
gtttaattac ccaagtttga gatgccttcc acaaggagac aacaggaggg cggaggtgca      60
gatgcggaaa cacataccgt ttacggtaca aatctgataa caaatcggaa tagccaagaa     120
gacgaaaatg ttgtggaaga agcggagctg aaatacggag catctcacgt tattcatcta     180
tttgtgccgg tgtcactatg catggctctg gttgttttta cgatgaacac gattacgttt     240
tatagtcaaa acaatggaag gcatttacta tcacatcctt ttgtccggga aacagacagt     300
atcgttgaga agggattgat gtcacttgga atgctctcg tcatgttgtg cgtggtcgtt      360
ctgatgacag ttctgctgat tgttttctat aaatacaagt tttataagct tattcatgga     420
tggcttattg tcagcagttt tcttcttctt ttcctattca ctacaatcta tgtgcaagaa     480
gttctgaaaa gtttcgatgt gtctcccagc gcactattgg ttttgtttgg actgggtaac     540
tatggagttc tcggaatgat gtgtatacat tggaaaggtc cattgcgtct gcaacagttc     600
taccttatta caatgtctgc actaatggct ctggtcttta tcaagtacct accagaatgg     660
actgtgtggt ttgtgctgtt tgttatctcg gtttgggatc tggttgccgt gctcacacca     720
aaaggaccat tgagatattt ggtggaaact gcacaggaga aaacgagcc aattttcccg      780 gcgctgattt attcgtctgg agtcatctat ccctacgttc ttgttactgc agttgaaaac     840
acgacagacc cccgtgaacc gacgtcgtca gactcaaata cttctacagc ttttcctgga     900
gaggcgagtt gttcatctga aacgccaaaa cggccaaaag tgaaacgaat tcctcaaaaa     960
gtgcaaatcg aatcgaatac tacagcttca acgacacaaa actctggagt aagggtggaa    1020
cgggagctag ctgctgagag accaactgta caagacgcca ttttcacag cacgaagag      1080 gaagagagag gtgtgaaact tggtctgggc gacttcattt tctactctgt tctcctcggc    1140
aaggcttcat cgtactttga ctggaacacg actatcgctt gttatgtggc cattcttatc    1200
ggtctctgct tcactcttgt cctgctcgcc gtcttcaaac gagcactccc ggctctgcaa    1260
tttccatttt ctccggactc attttttact tttgtacccg ctggatcatc accccatttg    1320
ttacacaagt ctctcaaaag tgtttattat attaattctc tgttttttgcc atttctttgc   1380 atcatcaact tttcgattat atcttgagcg atctcaaagc tttattttac atacctattt    1440 attttttgaac tttgtcattt aagttatata aataatttat taaaaaaaaa aaaaaaaaa    1500
```

<210> SEQ ID NO 6
<211> LENGTH: 461
<212> TYPE: PRT
<213> ORGANISM: C. elegans
<220> FEATURE:
<221> NAME/KEY: misc_feature
<223> OTHER INFORMATION: Fig. 2A Sel-12

<400> SEQUENCE: 6

```
Met Pro Ser Thr Arg Gln Gln Glu Gly Gly Gly Ala Asp Ala Glu
1               5                   10                  15

Thr His Thr Val Tyr Gly Thr Asn Leu Ile Thr Asn Arg Asn Ser Gln
            20                  25                  30

Glu Asp Glu Asn Val Val Glu Glu Ala Glu Leu Lys Tyr Gly Ala Ser
        35                  40                  45

His Val Ile His Leu Phe Val Pro Val Ser Leu Cys Met Ala Leu Val
    50                  55                  60

Val Phe Thr Met Asn Thr Ile Thr Phe Tyr Ser Gln Asn Asn Gly Arg
65                  70                  75                  80

His Leu Leu Ser His Pro Phe Val Arg Glu Thr Asp Ser Ile Val Glu
                85                  90                  95
```

-continued

```
Lys Gly Leu Met Ser Leu Gly Asn Ala Leu Val Met Leu Cys Val Val
            100                 105                 110
Val Leu Met Thr Val Leu Leu Ile Val Phe Tyr Lys Tyr Lys Phe Tyr
        115                 120                 125
Lys Leu Ile His Gly Trp Leu Ile Val Ser Ser Phe Leu Leu Leu Phe
    130                 135                 140
Leu Phe Thr Thr Ile Tyr Val Gln Glu Val Leu Lys Ser Phe Asp Val
145                 150                 155                 160
Ser Pro Ser Ala Leu Leu Val Leu Phe Gly Leu Gly Asn Tyr Gly Val
                165                 170                 175
Leu Gly Met Met Cys Ile His Trp Lys Gly Pro Leu Arg Leu Gln Gln
            180                 185                 190
Phe Tyr Leu Ile Thr Met Ser Ala Leu Met Ala Leu Val Phe Ile Lys
        195                 200                 205
Tyr Leu Pro Glu Trp Thr Val Trp Phe Val Leu Phe Val Ile Ser Val
    210                 215                 220
Trp Asp Leu Val Ala Val Leu Thr Pro Lys Gly Pro Leu Arg Tyr Leu
225                 230                 235                 240
Val Glu Thr Ala Gln Glu Arg Asn Glu Pro Ile Phe Pro Ala Leu Ile
                245                 250                 255
Tyr Ser Ser Gly Val Ile Tyr Pro Tyr Val Leu Val Thr Ala Val Glu
            260                 265                 270
Asn Thr Thr Asp Pro Arg Glu Pro Thr Ser Asp Ser Asn Thr Ser
        275                 280                 285
Thr Ala Phe Pro Gly Glu Ala Ser Cys Ser Ser Glu Thr Pro Lys Arg
    290                 295                 300
Pro Lys Val Lys Arg Ile Pro Gln Lys Val Gln Ile Glu Ser Asn Thr
305                 310                 315                 320
Thr Ala Ser Thr Thr Gln Asn Ser Gly Val Arg Val Glu Arg Glu Leu
                325                 330                 335
Ala Ala Glu Arg Pro Thr Val Gln Asp Ala Asn Phe His Arg His Glu
            340                 345                 350
Glu Glu Glu Arg Gly Val Lys Leu Gly Leu Gly Asp Phe Ile Phe Tyr
        355                 360                 365
Ser Val Leu Leu Gly Lys Ala Ser Ser Tyr Phe Asp Trp Asn Thr Thr
    370                 375                 380
Ile Ala Cys Tyr Val Ala Ile Leu Ile Gly Leu Cys Phe Thr Leu Val
385                 390                 395                 400
Leu Leu Ala Val Phe Lys Arg Ala Leu Pro Ala Leu Gln Phe Pro Phe
                405                 410                 415
Ser Pro Asp Ser Phe Phe Thr Val Pro Ala Gly Ser Ser Pro His
            420                 425                 430
Leu Leu His Lys Ser Leu Lys Ser Val Tyr Tyr Ile Asn Ser Leu Phe
        435                 440                 445
Leu Pro Phe Leu Cys Ile Ile Asn Phe Ser Ile Ile Ser
    450                 455                 460
```

<210> SEQ ID NO 7
<211> LENGTH: 21
<212> TYPE: DNA
<213> ORGANISM: C. elegans
<220> FEATURE:
<221> NAME/KEY: artificial_sequence
<222> LOCATION: (1)..(21)
<223> OTHER INFORMATION: primer or probe -continued

```
<210> SEQ ID NO 8
<211> LENGTH: 24
<212> TYPE: DNA
<213> ORGANISM: C. elegans
<220> FEATURE:
<221> NAME/KEY: artificial_sequence
<222> LOCATION: (1)..(24)
<223> OTHER INFORMATION: primer or probe

<400> SEQUENCE: 8
ggaatctgaa gcacctgtaa gcat                                           24

<210> SEQ ID NO 9
<211> LENGTH: 448
<212> TYPE: PRT
<213> ORGANISM: human
<220> FEATURE:
<221> NAME/KEY: misc_feature
<223> OTHER INFORMATION: Fig. 2A E5-1
<220> FEATURE:
<221> NAME/KEY: misc_feature
<223> OTHER INFORMATION: Fig. 2A E5-1/STM2

<400> SEQUENCE: 9
```

<400> SEQUENCE: 7
tgtctgagtt actagttttc c                                              21

Met Leu Thr Phe Met Ala Ser Asp Ser Glu Glu Val Cys Asp Glu
1               5                   10                  15

Arg Thr Ser Leu Met Ser Ala Glu Ser Pro Thr Pro Arg Ser Cys Gln
            20                  25                  30

Glu Gly Arg Gln Gly Pro Glu Asp Gly Glu Asn Thr Ala Gln Trp Arg
        35                  40                  45

Ser Gln Glu Asn Glu Glu Asp Gly Glu Glu Asp Pro Asp Arg Tyr Val
    50                  55                  60

Cys Ser Gly Val Pro Gly Arg Pro Pro Gly Leu Glu Glu Glu Leu Thr
65                  70                  75                  80

Leu Lys Tyr Gly Ala Lys His Val Ile Met Leu Phe Val Pro Val Thr
                85                  90                  95

Leu Cys Met Ile Val Val Val Ala Thr Ile Lys Ser Val Arg Phe Tyr
            100                 105                 110

Thr Glu Lys Asn Gly Gln Leu Ile Tyr Thr Pro Phe Thr Glu Asp Thr
        115                 120                 125

Pro Ser Val Gly Gln Arg Leu Leu Asn Ser Val Leu Asn Thr Leu Ile
    130                 135                 140

Met Ile Ser Val Ile Val Val Met Thr Ile Phe Leu Val Val Leu Tyr
145                 150                 155                 160

Lys Tyr Arg Cys Tyr Lys Phe Ile His Gly Trp Leu Ile Met Ser Ser
                165                 170                 175

Leu Met Leu Leu Phe Leu Phe Thr Tyr Ile Tyr Leu Gly Glu Val Leu
            180                 185                 190

Lys Thr Tyr Asn Val Ala Met Asp Tyr Pro Thr Leu Leu Leu Thr Val
        195                 200                 205

Trp Asn Phe Gly Ala Val Gly Met Val Cys Ile His Trp Lys Gly Pro
    210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
                245                 250                 255

-continued

```
Gly Ala Ile Ser Val Tyr Asp Leu Val Ala Val Leu Cys Pro Lys Gly
            260                 265                 270

Pro Leu Arg Met Leu Val Glu Thr Ala Gln Glu Arg Asn Glu Pro Ile
        275                 280                 285

Phe Pro Ala Leu Ile Tyr Ser Ser Ala Met Val Trp Thr Val Gly Met
    290                 295                 300

Ala Lys Leu Asp Pro Ser Ser Gln Gly Ala Leu Gln Leu Pro Tyr Asp
305                 310                 315                 320

Pro Glu Met Glu Glu Asp Ser Tyr Asp Ser Phe Gly Glu Pro Ser Tyr
                325                 330                 335

Pro Glu Val Phe Glu Pro Pro Leu Thr Gly Tyr Pro Gly Glu Glu Leu
            340                 345                 350

Glu Glu Glu Glu Glu Arg Gly Val Lys Leu Gly Leu Gly Asp Phe Ile
        355                 360                 365

Phe Tyr Ser Val Leu Val Gly Lys Ala Ala Thr Gly Ser Gly Asp
    370                 375                 380

Trp Asn Thr Thr Leu Ala Cys Phe Val Ala Ile Leu Ile Gly Leu Cys
385                 390                 395                 400

Leu Thr Leu Leu Leu Leu Ala Val Phe Lys Lys Ala Leu Pro Ala Leu
                405                 410                 415

Pro Ile Ser Thr Thr Phe Gly Leu Ile Phe Tyr Phe Ser Thr Asp Asn
            420                 425                 430

Leu Val Arg Pro Phe Met Asp Thr Leu Ala Ser His Gln Leu Tyr Ile
        435                 440                 445
```

```
<210> SEQ ID NO 10
<211> LENGTH: 27
<212> TYPE: DNA
<213> ORGANISM: human
<220> FEATURE:
<221> NAME/KEY: artifical_sequence
<222> LOCATION: (1)..(27)
<223> OTHER INFORMATION: sense primer for human PS1; pg 52

<400> SEQUENCE: 10
ggggtaccat gacagagtta cctgcac                                      27

<210> SEQ ID NO 11
<211> LENGTH: 25
<212> TYPE: DNA
<213> ORGANISM: human
<220> FEATURE:
<221> NAME/KEY: artifical_sequence
<222> LOCATION: (1)..(25)
<223> OTHER INFORMATION: antisense primer for human PS1; pg. 52

<400> SEQUENCE: 11
ccgggatcca tgggattcta accgc                                        25

<210> SEQ ID NO 12
<211> LENGTH: 27
<212> TYPE: DNA
<213> ORGANISM: human
<220> FEATURE:
<221> NAME/KEY: artificial_sequence
<222> LOCATION: (1)..(27)
<223> OTHER INFORMATION: PS1 M146L sense primer 1

<400> SEQUENCE: 12
gtcattgttg tcctgactat cctcctg                                      27
```

<210> SEQ ID NO 13
<211> LENGTH: 20
<212> TYPE: DNA
<213> ORGANISM: human
<220> FEATURE:
<221> NAME/KEY: artificial_sequence
<222> LOCATION: (1)..(20)
<223> OTHER INFORMATION: PS1 M146L antisense primer 1

<400> SEQUENCE: 13
gaggagtaaa tgagagctgg                                              20

<210> SEQ ID NO 14
<211> LENGTH: 27
<212> TYPE: DNA
<213> ORGANISM: human
<220> FEATURE:
<221> NAME/KEY: artificial_sequence
<222> LOCATION: (1)..(27)
<223> OTHER INFORMATION: PS1 M146L sense primer 2

<400> SEQUENCE: 14
caggaggata gtcaggacaa caatgac                                      27

<210> SEQ ID NO 15
<211> LENGTH: 19
<212> TYPE: DNA
<213> ORGANISM: human
<220> FEATURE:
<221> NAME/KEY: artificial_sequence
<222> LOCATION: (1)..(19)
<223> OTHER INFORMATION: PS1 M146L antisense primer 2

<400> SEQUENCE: 15
caggtggtgg agcaagatg                                               19

<210> SEQ ID NO 16
<211> LENGTH: 20
<212> TYPE: DNA
<213> ORGANISM: human
<220> FEATURE:
<221> NAME/KEY: artificial_sequence
<222> LOCATION: (1)..(20)
<223> OTHER INFORMATION: PS1 H163R primer

<400> SEQUENCE: 16
ctaggtcatc cgtgcctggc                                              20

<210> SEQ ID NO 17
<211> LENGTH: 20
<212> TYPE: DNA
<213> ORGANISM: human
<220> FEATURE:
<221> NAME/KEY: artificial_sequence
<222> LOCATION: (1)..(20)
<223> OTHER INFORMATION: PS1 H163R primer

<400> SEQUENCE: 17
gccaggcacg gatgacctag                                              20

<210> SEQ ID NO 18
<211> LENGTH: 26
<212> TYPE: DNA
<213> ORGANISM: human
<220> FEATURE:
<221> NAME/KEY: artificial_sequence
<222> LOCATION: (1)..(26)
<223> OTHER INFORMATION: PS1 L286V primer -continued

```
<400> SEQUENCE: 18 cgcttttttcc agctgtcatt tactcc                                     26

<210> SEQ ID NO 19
<211> LENGTH: 27
<212> TYPE: DNA
<213> ORGANISM: human
<220> FEATURE:
<221> NAME/KEY: artificial_sequence
<222> LOCATION: (1)..(27)
<223> OTHER INFORMATION: PS1 L286V primer

<400> SEQUENCE: 19
ccggaattct caggttgtgt tccagtc                                     27

<210> SEQ ID NO 20
<211> LENGTH: 26
<212> TYPE: DNA
<213> ORGANISM: human
<220> FEATURE:
<221> NAME/KEY: artificial_sequence
<222> LOCATION: (1)..(26)
<223> OTHER INFORMATION: PS1 L286V primer

<400> SEQUENCE: 20
ggagtaaatg acagctggaa aaagcg                                      26

<210> SEQ ID NO 21
<211> LENGTH: 24
<212> TYPE: DNA
<213> ORGANISM: human
<220> FEATURE:
<221> NAME/KEY: artificial_sequence
<222> LOCATION: (1)..(24)
<223> OTHER INFORMATION: PS1 L286V primer

<400> SEQUENCE: 21
ggatccattg ttgtcatgac tatc                                        24

<210> SEQ ID NO 22
<211> LENGTH: 23
<212> TYPE: DNA
<213> ORGANISM: human
<220> FEATURE:
<221> NAME/KEY: artificial_sequence
<222> LOCATION: (1)..(23)
<223> OTHER INFORMATION: PS1 C410Y primer

<400> SEQUENCE: 22
caaccatagc ctatttcgta gcc                                         23

<210> SEQ ID NO 23
<211> LENGTH: 33
<212> TYPE: DNA
<213> ORGANISM: human
<220> FEATURE:
<221> NAME/KEY: artificial_sequence
<222> LOCATION: (1)..(33)
<223> OTHER INFORMATION: PS1 C410Y primer

<400> SEQUENCE: 23
gccagtgaat tgtaatacga ctcactatag ggc                              33

<210> SEQ ID NO 24
<211> LENGTH: 23
<212> TYPE: DNA
```

-continued

```
<213> ORGANISM: human
<220> FEATURE:
<221> NAME/KEY: artificial_sequence
<222> LOCATION: (1)..(23)
<223> OTHER INFORMATION: PS1 C410Y primer

<400> SEQUENCE: 24
ggctacgaaa taggctatgg ttg                                         23

<210> SEQ ID NO 25
<211> LENGTH: 24
<212> TYPE: DNA
<213> ORGANISM: human
<220> FEATURE:
<221> NAME/KEY: artificial_sequence
<222> LOCATION: (1)..(24)
<223> OTHER INFORMATION: PS1 C410Y primer

<400> SEQUENCE: 25
ccggaattct gaatggactg cgtg                                        24

<210> SEQ ID NO 26
<211> LENGTH: 27
<212> TYPE: DNA
<213> ORGANISM: human
<220> FEATURE:
<221> NAME/KEY: artificial_sequence
<222> LOCATION: (1)..(27)
<223> OTHER INFORMATION: PS2 primer

<400> SEQUENCE: 26
ccggtaccaa gtgttcgtgg tgcttcc                                     27

<210> SEQ ID NO 27
<211> LENGTH: 29
<212> TYPE: DNA
<213> ORGANISM: human
<220> FEATURE:
<221> NAME/KEY: artificial_sequence
<222> LOCATION: (1)..(29)
<223> OTHER INFORMATION: PS2 primer

<400> SEQUENCE: 27
ccgtctagac ctcagatgta gagctgatg                                   29
```